United States Patent
Doutova et al.

(10) Patent No.: US 7,888,505 B2
(45) Date of Patent: Feb. 15, 2011

(54) 6,7-DIHYDROBENZIMIDAZO[1,2-C]QUINAZOLIN-6-ONE CARBOXYLIC ACIDS, THEIR ESTERS, AND METHODS OF SYNTHESIS THEREOF

(75) Inventors: Tatyana Doutova, Moscow (RU); Pavel I. Lazarev, London (GB); Elena N. Sidorenko, Moscow (RU); Valery S. Kuzmin, Moscow (RU)

(73) Assignee: Crysoptix, KK, Tokyo (JP)

( * ) Notice: Subject to any disclaimer, the term of this patent is extended or adjusted under 35 U.S.C. 154(b) by 303 days.

(21) Appl. No.: 12/160,410

(22) PCT Filed: Jan. 15, 2007

(86) PCT No.: PCT/GB2007/000102

§ 371 (c)(1),
(2), (4) Date: Oct. 7, 2008

(87) PCT Pub. No.: WO2007/080420

PCT Pub. Date: Jul. 19, 2007

(65) Prior Publication Data

US 2010/0047477 A1   Feb. 25, 2010

(30) Foreign Application Priority Data

Jan. 13, 2006  (GB) ................. 0600763.7

(51) Int. Cl.
C07D 471/00 (2006.01)
C07D 487/00 (2006.01)
C07D 491/00 (2006.01)

(52) U.S. Cl. .................................... 544/247
(58) Field of Classification Search .................. 544/247
See application file for complete search history.

(56) References Cited

U.S. PATENT DOCUMENTS

| 5,739,296 | A | 4/1998 | Gvon et al. |
| 6,174,394 | B1 | 1/2001 | Gvon et al. |
| 2004/0058091 | A1* | 3/2004 | Dutova et al. ............. 428/1.1 |
| 2004/0233528 | A1 | 11/2004 | Lazarev et al. |
| 2006/0062932 | A1 | 3/2006 | Dutova et al. |

FOREIGN PATENT DOCUMENTS

EP   0961138 A1   12/1991

WO   2004/003599 A2   1/2004

OTHER PUBLICATIONS

Bahadur, "Liquid Crystals—Applications and Uses," vol. 1, p. 101, World Scientific, Singapore—New York, 1990.
Nazarov et al., "Electronic Spectra of Aqueous Solutions and Films Made of Liquid Crystal Ink for Thin Film Polarizers," Molecular Materials, 2001, vol. 14, No. 2, pp. 153-163.
Remizov et al., "Rheology of The Lyotropic Liquid Crystalline Material for Thin Film Polarizers," Molecular Materials, 2001, vol. 14, No. 2, pp. 179-190.
Lydon, "Chromonics," Handbook of Liquid Crystals,1998, vol. 2B, p. 981-1007, Wiley VCH, Weinheim.
Yeh et al., "Optical Waves in Layered Media," New York, John Wiley & Sons, 2010.
Lazarev et al., "Thin Crystal Film Retarders," Proceeding of the 7th International Display Workshops, Materials and Components, Nov. 29-Dec. 1, 2000, Kobe, Japan, pp. 1159-1160.
Fiske et al., "Molecular Alignment in Crystal Polarizers and Retarders," Society for Information Display Int. Symp., Digest of Technical Papers, May 19-24, 2002, Boston, MA, pp. 866-869.
PCT, International Search Report and Written Opinion of the International Searching Authority in PCT/GB2007/000102, May 25, 2007, 10 pages.

* cited by examiner

*Primary Examiner*—James O Wilson
*Assistant Examiner*—Erich A Leeser
(74) *Attorney, Agent, or Firm*—Houst Consulting

(57) ABSTRACT

The present invention relates to a 6,7-dihydrobenzimidazo[1,2-c]quinazolin-6-one carboxylic acid and its esters of the general structural formula (I), and provides a method for their synthesis (I) where R and each R' are selected independently from the list comprising —H—$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; n is 1, 2, 3 or 4; Y is a substituent selected from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —NHCOCH$_3$; and z is 0, 1, 2, 3 or 4.

(I)

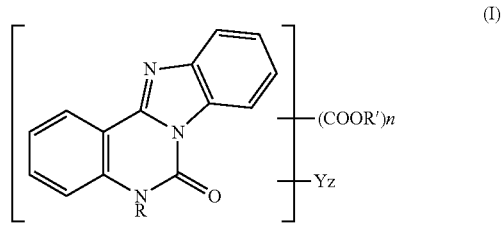

55 Claims, No Drawings

6,7-DIHYDROBENZIMIDAZO[1,2-C]QUINAZOLIN-6-ONE CARBOXYLIC ACIDS, THEIR ESTERS, AND METHODS OF SYNTHESIS THEREOF

The present invention relates generally to the field of organic chemistry and particularly to the field of heterocyclic compounds. More specifically, the present invention is related to carboxylic acids and esters, in particular, to 6,7-dihydrobenzimidazo[1,2-c]quinazolin-6-one carboxylic acids, their esters, and methods of synthesis thereof.

Liquid crystals are widely used in electronics as optical display elements. The contrast, colour reproduction (colour rendering), and stable grey scale intensity gradation are important quality characteristics of electronic displays employing liquid crystal technology—Liquid Crystal Displays (LCD). The primary factor determining the contrast of LCD is the propensity for light to "leak" through liquid crystal elements or cells, which are in the dark or "black" pixel state. In addition, the optical leakage and, hence, the contrast of an LCD also depend on the direction from which the display screen is viewed.

LCDs are now replacing CRTs as monitors for in multiple different applications. It is expected that the proportion of LCD television monitors with a larger screen size will also sharply increase in the nearest future. However, unless problems related to the effect of viewing angle on the colour reproduction, contrast degradation, and brightness inversion are solved, the replacement of traditional CRTs by LCDs will be limited.

The type of optical compensation required depends on the type of display used in each particular system. In a normally black display, the twisted nematic cell is placed between polarizers whose transmission axes are parallel to one another and to the orientation of the liquid crystal director at the rear surface of the cell (i.e., at the cell side that is away from the viewer). In the unenergized state (zero applied voltage), normally incident light from the backlight system is polarized by the first polarizer and transmitted through the cell with the polarization direction rotated by the twist angle of the cell. The twist angle is set to 90 DEG so that the output polarizer (analyzer) blocks this light. Patterns can be written in the display by selectively applying a voltage to the portions of the display that are to appear illuminated.

However, when viewed at large angles, the dark (unenergized) areas of a normally black display will appear bright because of the angle-dependent retardation effect for the light rays passing through the liquid crystal layer at such angles, whereby off-normal incident light exhibits an angle-dependent change in the polarization. The contrast can be restored by using a compensating element, which has an optical symmetry similar to that of a twist cell but produces the reverse effect. This can be solved with the different methods developed in the LCD industry Thus, the technological progress poses the task of developing optical elements based on new materials with desired controllable properties. In particular, important optical elements in modern visual display systems are optically anisotropic films with optical characteristics optimised for use in a particular display module.

Various polymeric materials are known in the prior art, which are intended for use in the production of optically anisotropic films. Films based on these polymers acquire optical anisotropy through uniaxial extension and coloration with organic or inorganic (iodine) dyes. Poly(vinyl alcohol) (PVA) is among polymers that are widely used for this purpose. However, a relatively low thermal stability of PVA based films limits their applications. PVA based films are described in greater detail in the monograph *Liquid Crystals—Applications and Uses*, B. Bahadur (ed.), World Scientific, Singapore-New York (1990), Vol. 1, p. 101.

Organic dichroic dyes constitute a new class of materials currently gaining prominence in the manufacture of optically anisotropic films with desirable optical and working characteristics. Films based on these materials can be obtained by applying an aqueous liquid crystal (LC) solution of supramolecules containing dye molecules onto a substrate surface, with the subsequent evaporation of water.

A hydrophobic-hydrophilic balance of molecules of polycyclic organic compounds makes them soluble in water and stimulates their self-assembly into supramolecules. Organic compounds in water form a colloid system or lyotropic liquid crystal, where molecules aggregate into supramolecules and these supramolecules represent kinetic units of the colloidal system (see, P. I. Lazarev, M. V. Paukshto, "Multilayer optical coating," U.S. 2004/0233528 (2004)). Spectral characteristics and rheological properties of materials (see, V. Nazarov, L. Ignatov, K. Kienskaya, "Electronic Spectra of Aqueous Solutions and Films Made of Liquid Crystal Ink for Thin Film Polarizers," *Molecular Materials*, Vol. 14, No. 2, pp. 153-163 (2001); S. Remizov, A. Krivoshchepov, V. Nazarov, A. Grodsky, "Rheology of The Lyotropic Liquid Crystalline Material for Thin Film Polarizers," *Molecular Materials*, Vol. 14, No. 2, pp. 179-190 (2001)) indicate strong tendency of these molecules to aggregate, even in diluted aqueous solutions, with formation of supramolecules with columnar structure. Columnar structure is specific for flat shaped molecules grouped in "face-to-face" fashion with hydrophobic molecular planar cores of aromatic conjugated bond system stacked on each other inside of the supramolecule's core and the hydrophilic peripheral groups exposed to water. Water provides the medium for electrostatic interaction and mutual alignment of supramolecules with resulting lyotropic liquid crystal structure of certain symmetry at certain level of aggregates concentration. Formation of supramolecules starts at low concentration of amphiphilic compounds in the water. There are two types of data that can be used as a basis for previous statement which are (1) optical spectra of molecular compounds that are building block of supramolecules, and (2) light scattering data that correlate with size of aggregates that are present in the system.

The applied films are rendered anisotropic either by preliminary mechanical orientation of the substrate surface or by post-treatment using external mechanical, electromagnetic, or other orienting forces applied to the LC film material on the substrate.

Liquid crystal properties of dye solutions are well known. In recent years, use of liquid crystals based of such dye solutions for commercial applications such as LCDs and glazing coatings has received much attention.

Dye supramolecules form lyotropic liquid crystals (LLCs). Substantial molecular ordering or organization of dye molecules in the form of columns allows such supramolecular LC mesophases to be used for obtaining oriented, strongly dichroic films.

Dye molecules forming supramolecular LC mesophases possess unique properties. These dye molecules contain functional groups located at the periphery, which render these molecules soluble in water. Organic dye mesophases are characterized by specific structures, phase diagrams, optical properties, and solubility as described in greater detail in: J. Lydon, Chromonics, in *Handbook of Liquid Crystals*, Wiley VCH, Weinheim (1998), Vol. 2B, p. 981-1007 (see also references therein).

Anisotropic films characterized by high optical anisotropy can be formed from LLC systems based on dichroic dyes. Such films exhibit the properties of so-called E-type polarizers (due to the absorption of light by supramolecular complexes). Organic conjugated compounds with the general molecular structure similar to that of dye molecules, but exhibiting no absorption in the visible spectral range, can be used as retarders and compensators.

Retarders and compensators are the films possessing phase-retarding properties in the spectral regions where the optical absorption is absent. The phase-retarding or compensating properties of such films are determined by their double refraction also known as birefringence ($\Delta n$):

$$\Delta n = |n_o - n_e|,$$

which is the difference of the refractive indices for the extraordinary wave ($n_e$) and the ordinary wave ($n_o$). The $n_e$ and $n_o$ values vary depending on the orientation of molecules in a medium and on the direction of light propagation. For example, if this direction coincides with the optical or crystallographic axis, the ordinary polarization is predominantly observed. If the light propagates in the perpendicular direction or at some angle to the optical axis, the light emerging from the medium will separate into extraordinary and ordinary components.

It is also important to note that, in addition to the unique optical properties, the films based on organic aromatic compounds are characterized by a high thermal stability and radiation resistance (photostability).

There is increasing demand for anisotropic films with improved selectivity in various wavelength ranges. Films exhibiting different optical absorption maxima over a wide spectral interval ranging from infrared (IR) to ultraviolet (UV) regions are required for a variety of technological applications. Hence, much recent research attention has been directed to the synthesis of new materials for the manufacture of isotropic and/or anisotropic birefringent films, polarizers, retarders or compensators (herein collectively referred to as optical materials or films) for LCD and telecommunication applications, such as (but not limited to) those described in P. Yeh, *Optical Waves in Layered Media*, New York, John Wiley & Sons (1998) and in P. Yeh and C. Gu, *Optics of Liquid Crystal Displays*, New York, John Wiley & Sons, (1999).

It has been found that ultrathin birefringent films can be fabricated using the known methods and technologies developed for the production of optically anisotropic films based on organic dye LLC systems. For example, the manufacture of thin, optically anisotropic crystalline films based on disulfoacids of the red dye Vat Red 14 has been described by P. Lazarev and M. Paukshto, Thin Crystal Film Retarders (in: *Proceeding of the 7th International Display Workshops, Materials and Components*, Kobe, Japan, Nov. 29-Dec. 1, 2000, pp. 1159-1160) In particular, such films can be obtained using cis- and trans-isomer mixtures of naphthalenetetracarboxylic acid dibenzimidazole:

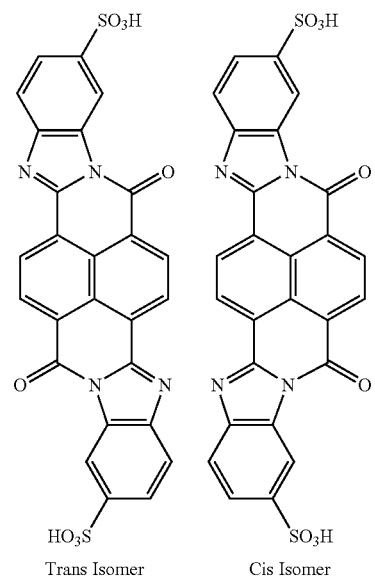

Trans Isomer      Cis Isomer

This technology makes it possible to control the direction of the crystallographic axis of a film during the deposition and crystallization of LC molecules on a substrate (e.g., on a glass plate). The obtained films have uniform compositions and are characterized by high molecular and/or crystal ordering, with a dichroic ratio of approximately $K_d \sim 28$, which makes them useful optical materials, in particular, for polarizers, retarders, and birefringent films or compensators.

Thin birefringent films transparent in the visible spectral range have been also obtained based on disodium chromoglycate (DSCG):

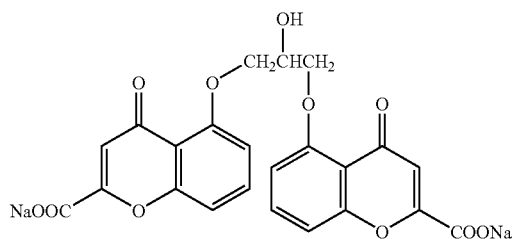

The anisotropy of oriented films made of DSCG is not very high: a difference in the refractive indices $\Delta n$ is in the visible range is approximately 0.1 to 0.13. However, the thicknesses of films based on DSCG can be varied over a wide range, thus making possible the preparation of films with desired phase-retarding properties despite low specific anisotropy characteristics of the material. These films are considered in greater detail in T. Fiske et al., Molecular Alignment in *Crystal Polarizers and Retarders: Society for Information Display Int. Symp.* (*Boston, Mass., May* 19-24 (2002), *Digest of Technical Papers*), pp. 566-569. The main disadvantage of many of these films is their dynamic instability, which leads to gradual recrystallization of the LC molecules and the resulting degradation of the optical anisotropy.

Other anisotropic film materials, based on water-soluble organic dyes, have been also obtained using the aforementioned technology; see, for example, U.S. Pat. Nos. 5,739,296 and 6,174,394 and European patent EP 0961138. However, such materials exhibit high optical absorption in the visible spectral range, which limits their use in applications requiring transparent birefringent films.

Still other anisotropic materials have been synthesized based on acenaphtho[1,2-b]quinoxaline sulfoderivatives having the general structural formula

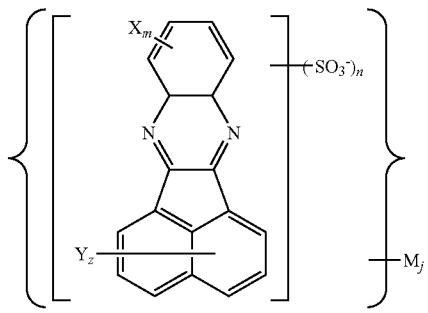

where n is an integer in the range from 1 to 4; m is an integer in the range from 0 to 4; z is an integer in the range from 0 to 6; m+z+n≦10; X and Y are molecular fragments individually selected from the list including $CH_3$, $C_2H_5$, $OCH_3$, $OC_2H_5$, Cl, Br, OH, $OCOCH_3$, $NH_2$, $NHCOCH_3$, $NO_2$, F, $CF_3$, CN, OCN, SCN, COOH, and $CONH_2$; M is a counter ion; and j is the number of counter ions in the molecule; with a proviso that, when n=1 and $SO_3$— occupies position 1, then m≠0 or z≠0.

Thus, there is a general need for films, which are optically anisotropic and sufficiently transparent in the spectral regions in which they are intended to operate. In particular, there is a need for such optical films transparent in the visible spectral range. It is therefore desirable to provide improved methods for the synthesis and manufacture of optically anisotropic films. It is also desirable to provide optical films resistant to humidity and temperature variations.

Until now, not much attention has been paid to 6,7-dihydrobenzimidazo[1,2-c]quinazolin-6-one ring system. Since similar compounds (6-oxypyrines) have proved to be of considerable interest from the standpoint of biological processes and since they form sparingly soluble silver salts, thus being suited for photographic applications (i.e., as crystal growth modifiers of silver halide grains, stabilizers, antifogging and antibronzing agents), further research on this ring system is expedient.

In particular, the disclosed chemical compounds may be used for the producing of the film or as an intermediate for the synthesis of the compounds which may be used for producing the optical films.

Several methods have been described in the literature for obtaining 6,7-dihydrobenzimidazo[1,2-c]quinazolin-6-one and its derivatives. According to the first method (see Scheme 1), 2-(o-aminophenyl)-benzimidazole undergoes cyclization under the action of phosgene, urea, or chloroformates, or transforms into a Schiff base, which is cyclized into the target compound by oxidation (see Niementowski; Chem. Ber.; 32; 1899; 1477).

Scheme 1.
Synthesis of 6,7-dihydrobenzimidazol[1,2-c]quinazolin-6-one from 2-(o-aminophenyl)-benzimidazole.

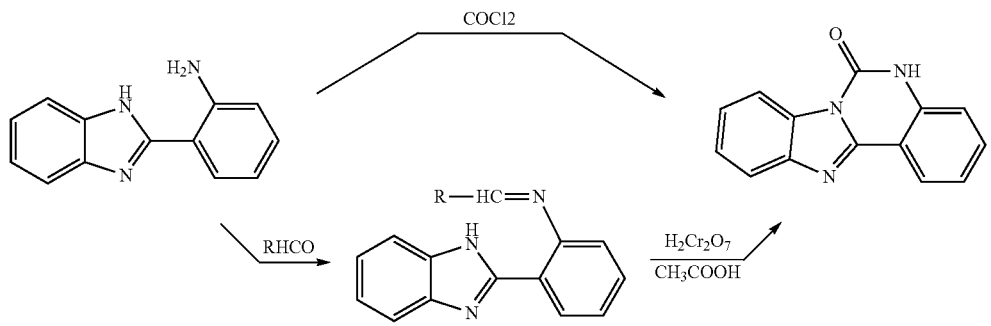

According to the second method (see Scheme 2), 6,7-dihydrobenzimidazo[1,2-c]quinazolin-6-one is synthesized from isatoic anhydride and o-phenylenediamine, but the yield is very low—approximately within 10-15% (see Taylor; Yoneda; Angew. Chem.; 79; 1967; 901; and 3. Padmaja, J.; Reddy, M. Satyanarayana; Ratnam, C. V.; Indian J. Chem. Sect. B; EN; 26; 1-12; 1987; 951-954).

Scheme 2.
Synthesis of 6,7-dihydrobenzimidazo[1,2-c]quinazolin-6-one from isatoic anhydride and o-diamines.

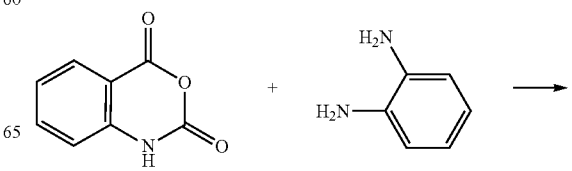

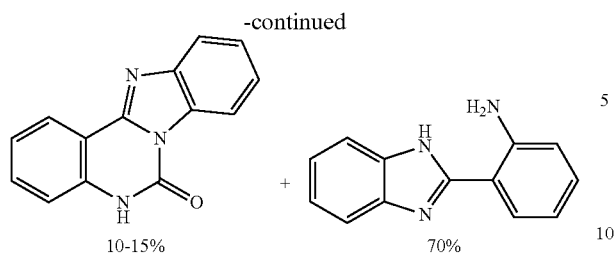

10-15%    70%

According to still another method, 6,7-dihydrobenzimidazo[1,2-c]quinazolin-6-one is obtained using a multistage procedure via isocyanates, whereby 2-isocyanobenzoyl chloride is converted into methyl anthranylate with a yield of 23% (Scheme 3) (see Beam et al.; J. Heterocycl. Chem.; 13; 1976; 421) and this intermediate compound transforms via 2-isocyanoanthranylate to give 5H-benzo[4,5]imidazo[1,2-c]quinazolin-6-one with a yield of 9% (Scheme 4) (see Lunn, W. H. W. and Harper, R. W.; J. Heterocycl. Chem.; EN; 8; 1971; 141-147).

Scheme 3.
Synthesis of 6,7-dihydrobenzimidazo[1,2-c]quinazolin-6-one from 2-isocyanobenzoyl chloride.

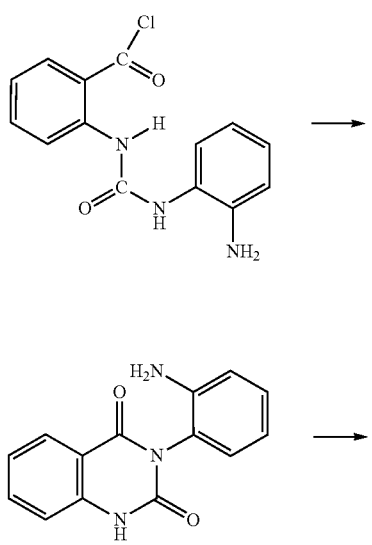

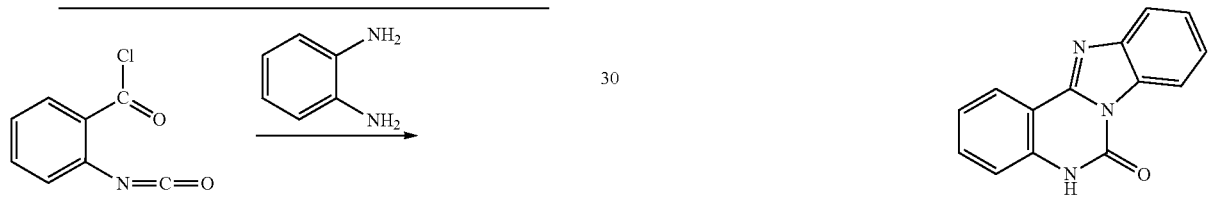

Scheme 4.
Synthesis of 6,7-dihydrobenzimidazol[1,2-c]quinazolin-6-one from methyl anthranylate.

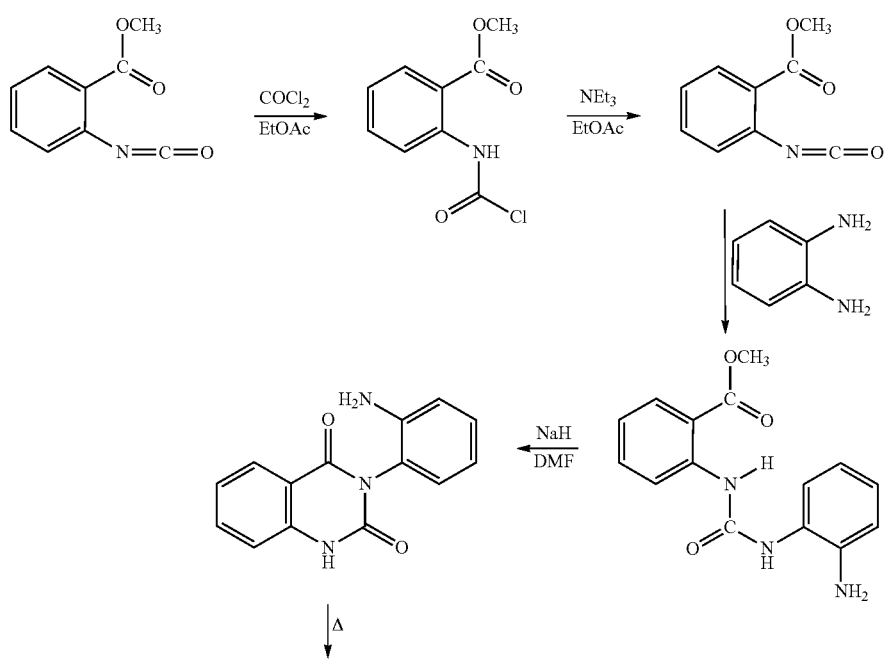

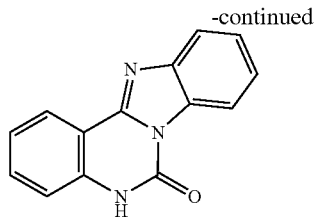

According to schemes 1-4, the target 6,7-dihydrobenzimidazo[1,2-c]quinazolin-6-one derivatives are obtained with low overall yield and, except for some procedures, require handling toxic reagents (phosgene).

Alternatively, 6,7-dihydrobenzimidazo[1,2-c]quinazolin-6-one derivatives can be obtained (see Scheme 5) proceeding from the initial 6,7-dihydrobenzimidazo[1,2-c]quinazoline-6-thiones (see Leistner, S., Wagner G., and Strohscheidt, Th.; Pharmazie; GE; 35; 5/6; 1980; 293-296), but this pathway is also multistage and low effective.

Scheme 5.
Synthesis of 6,7-dihydrobenzimidazo[1,2-c]quinazolin-6-one from 6,7-dihydrobenzimidazo[1,2-c]quinazolin-6-thiones

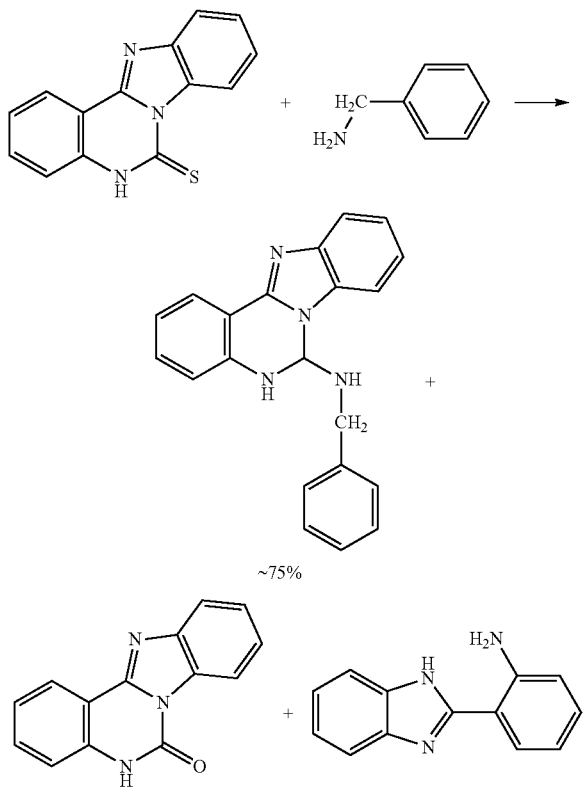

In the first aspect, the present invention provides a 6,7-dihydrobenzimidazo[1,2-c]quinazoline-6-one carboxylic acid and its esters of the general structural formula

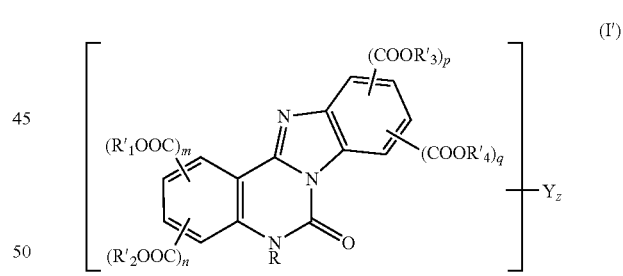

where R and each R' are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$, n is 1, 2, 3 or 4, Y is a substituent selected independently from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$, and z is 0, 1, 2, 3 or 4.

In preferred embodiments, the 6,7-dihydrobenzimidazo[1,2-c]quinazolin-6-one carboxylic acids and esters thereof have the general structural formula $$(I')$$

where R and $R'_1$, $R'_2$, $R'_3$, $R'_4$ are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; m, n, p and q is 0 or 1; (m+n+p+q) is equal or more than 1; Y is a substituent selected from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$; and z is 0, 1, 2, 3 or 4.

In the second aspect, the present invention provides a method for the synthesis of a 6,7-dihydrobenzimidazo[1,2-c]quinazolin-6-one carboxylic acid and its esters of the general structural formula

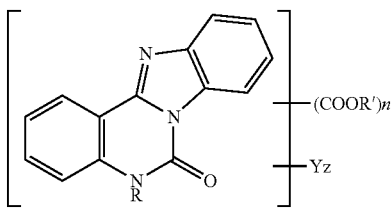

(I)

where R and each R' are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; n is 1, 2, 3 or 4; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of reacting in the presence of an oxidant a component of the formula (II):

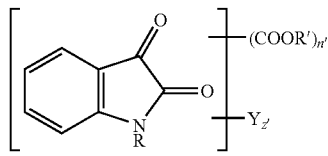

(II)

where n' is 0, 1 or 2, z' is 0, 1 or 2;
with a component of the formula (III):

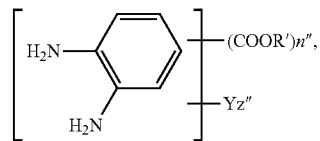

(III)

where n" is 0, 1 or 2, z" is 0, 1 or 2, and n'+n"≧1.

In preferred embodiments, there is provided a method of synthesis of a 6,7-dihydrobenzimidazo[1,2-c]quinazolin-6-one carboxylic acid and esters thereof of the general structural formula

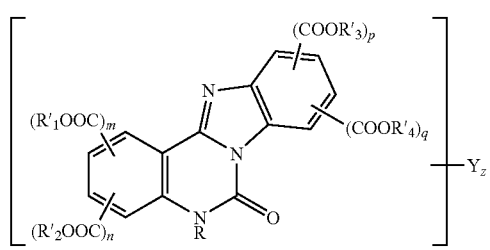

(I')

where R and R'$_1$, R'$_2$, R'$_3$, R'$_4$ are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; m, n, p and q is 0 or 1; (m+n+p+q) is equal or more than 1; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of reacting in the presence of an oxidant a component of the formula (II'):

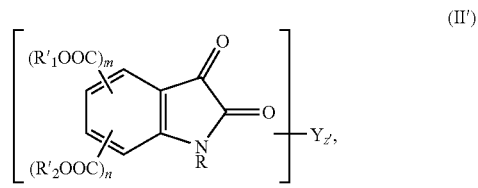

(II')

where z' is 0, 1 or 2; with a component of the formula (III'):

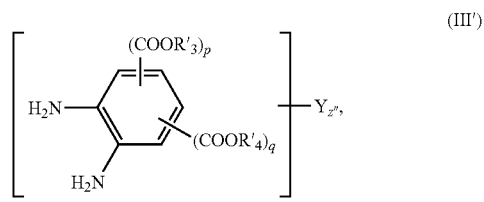

(III')

where z" is 0, 1 or 2;

In the third aspect, the present invention provides a method for the synthesis of a 6,7-dihydrobenzimidazo[1,2-c]quinazolin-6-one carboxylic acid and its esters of the general structural formula

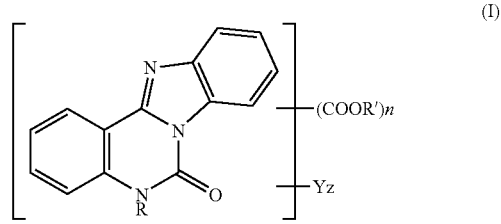

(I)

where R and each R' are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; n is 1, 2, 3 or 4; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of:

(a) preparing a mixture comprising a solvent; a component selected from the group including isatin and its derivatives of the general structural formula (II),

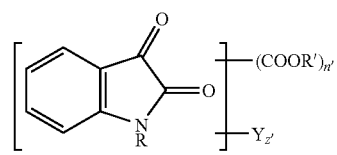

(II)

where n' is 0, 1 or 2, and z' is 0, 1 or 2;

and a component selected from the group consisting of o-phenylenediamine and its derivatives of the general structural formula (III):

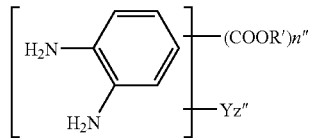
(III)

where n" is 0, 1 or 2, z" is 0, 1 or 2, and n'+n"≧1;

(b) treating said mixture with an oxidant;

(c) allowing the reaction to progress; and (d) isolating the 6,7-dihydrobenzimidazo[1,2-c]quinazolin-6-one carboxylic acid and its esters from the reaction mass.

In preferred embodiments, there is provided a method of synthesis of a 6,7-dihydrobenzimidazo[1,2-c]quinazolin-6-one carboxylic acid and esters thereof of the general structural formula

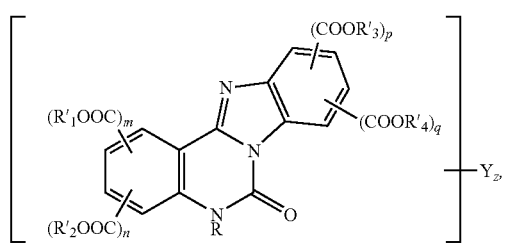
(I')

where R and R'$_1$, R'$_2$, R'$_3$, R'$_4$ are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; m, n, p and q is 0 or 1; (m+n+p+q) is equal or more than 1; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of:

(a) preparing a mixture comprising a solvent, a component selected from the group including isatin and its derivatives of the general structural formula (II'),

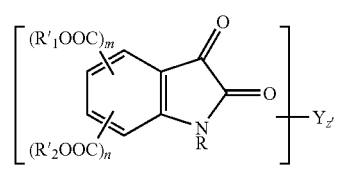
(II')

where z' is 0, 1 or 2;

and a component selected from the group consisting of o-phenylenediamine and its derivatives of the general structural formula (III'):

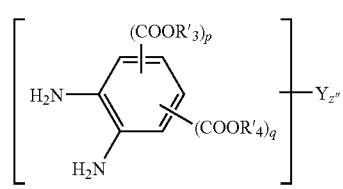
(III')

where z" is 0, 1 or 2;

(b) treating said mixture with an oxidant;

(c) allowing the reaction to progress; and (d) isolating the compound from the reaction mass.

In the fourth aspect, the present invention provides a method for the synthesis of a 6,7-dihydrobenzimidazo[1,2-c]quinazolin-6-one carboxylic acid and its esters of the general structural formula

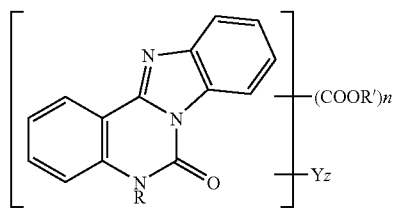
(I)

where R and each R' is selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$, n is 1, 2, 3 or 4, Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$, and z is 0, 1, 2, 3 or 4, which comprises the following steps:

(a) preparing a mixture consisting of a solvent; hydrochloric acid; a component selected from the group including isatin and its derivatives of the general structural formula (II),

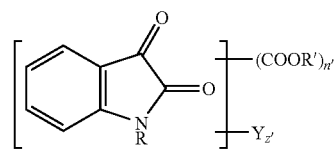
(II)

where n' is 0, 1 or 2, and z' is 0, 1 or 2;

and a component selected from the group consisting of o-phenylenediamine and its derivatives of the general structural formula (III),

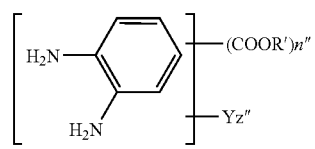
(III)

where n" is 0, 1 or 2, z" is 0, 1 or 2, and n'+n"≧1;

(b) treating said mixture with an oxidant selected from the group of inorganic and organic peroxides at a reaction temperature not higher than the temperature of side reactions;

(c) stirring the obtained reaction mass at the reaction temperature until the reaction is completed; and
(d) isolating the compound from the reaction mass.

In preferred embodiments, there is provided a method of synthesis of a 6,7-dihydrobenzimidazo[1,2-c]quinazolin-6-one carboxylic acid and esters thereof of the general structural formula

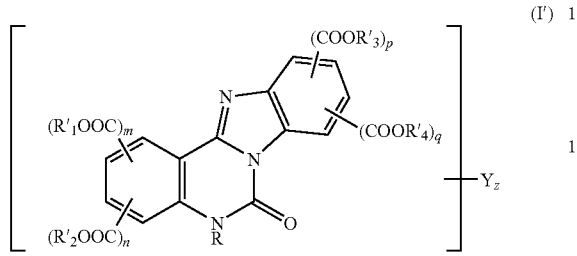

(I')

where R and $R'_1$, $R'_2$, $R'_3$, $R'_4$ are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; m, n, p and q is 0 or 1; (m+n+p+q) is equal or more than 1; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4.

The method comprises the following steps:
(a) preparing a mixture comprising a solvent; hydrochloric acid; a component selected from the group including isatin and its derivatives of the general structural formula (II')

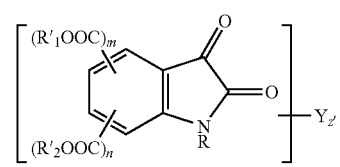

(II')

where z' is 0, 1 or 2;

and a component selected from the group consisting of o-phenylenediamine and its derivatives of the general structural formula (III')

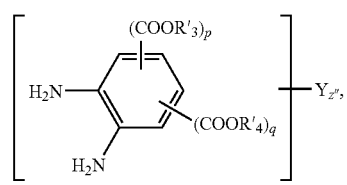

(III')

where z" is 0, 1 or 2;

(b) treating said mixture with an oxidant selected from the group of inorganic and organic peroxides at a reaction temperature not higher than the temperature of side reactions;
(c) stirring the obtained reaction mass at the reaction temperature until the reaction is completed; and
(d) isolating the compound from the reaction mass.

Thus, the present invention provides the method of preparing 6,7-dihydrobenzimidazo[1,2-c]quinazolin-6-one carboxylic acids and esters thereof of the general structural formulas (I) and (I'). The method is distinguished by a high yield and the use of inexpensive starting materials such as isatin and its derivatives and o-phenylenediamine and its derivatives according to Scheme 6.

Scheme 6.
Synthesis of 6,7-dihydrobenzimidazo[1,2-c]quinazolin-6-one carboxylic acids and esters thereof from isatin and o-phenylenediamine derivatives.

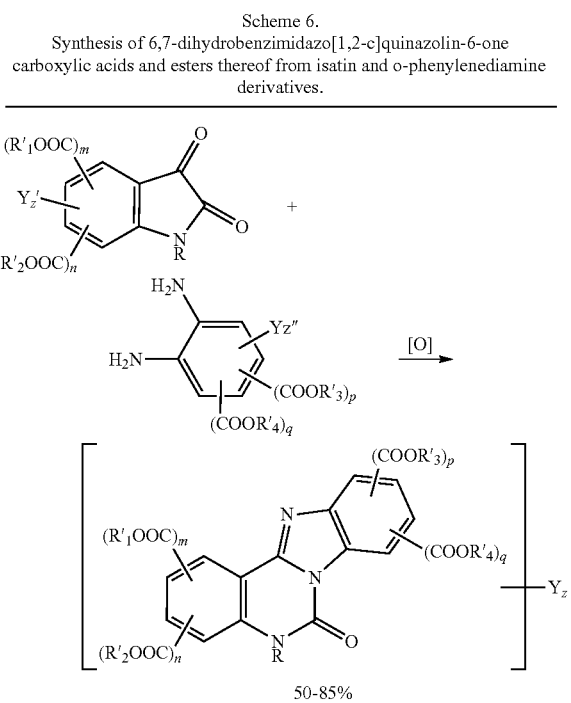

50-85%

The solvents used are selected from the group comprising water, and various mixtures of water and one or more organic solvents such as acetic acid and dimethylsulfoxide. Inorganic or organic peroxides such as hydrogen peroxide (H$_2$O$_2$), peroxyacetic acid (CH$_3$COOOH), and potassium peroxydisulfate (K$_2$S$_2$O$_8$) may be used as oxidants. All said oxidants and solvents are compatible. It is preferable to carry out the reaction in the presence of hydrochloric acid. The molar ratio of components II and III is selected in the range from 1:0.8 to 1:1.2, and it is most preferable to select this ratio equal to 1:1. In turn, the oxidant is preferably introduced in an amount not lower than 0.5 mole per mole of isatin or derivative thereof of the general structural formula (II) or (II'). It is most preferable that the oxidant is used in an amount of 1 mole per mole of isatin or derivative thereof of the general structural formula (II) or (II').

The temperature of side reactions means the temperature when the rate of by-product formation is higher than the rate of main reaction. The side reactions are the oxidation of o-phenylenediamine (or derivative thereof), the oxidation of satin (or derivative thereof) into the corresponding isatoic anhydrides, and the formation of heterocyclic compounds 10H-pyrido[4',3',5,6]-pyrazino[2,3-b]indoles of yellow color.

The conditions of synthesis are selected so as to obtain 6,7-dihydrobenzimidazo[1,2-c]quinazolin-6-one carboxylic acids and esters thereof of high purity (the main product content is 95-98.5%) immediately upon isolation from the reaction mass.

The target product is obtained in one step of a short duration: as a rule, the reaction is over within 1-2 hours. The disclosed method does not require any special conditions during the reaction. The product obtained has good filterability. All the starting materials are inexpensive and readily available on the market.

The general description of the present invention having been made, a further understanding can be obtained by reference to the specific preferred embodiments, which are given herein only for the purpose of illustration and are not intended to limit the scope of the appended claims.

In a first preferred embodiment, the present invention provides a 6,7-dihydrobenzimidazo[1,2-c]quinazolin-6-one carboxylic acid and esters thereof of the general structural formula

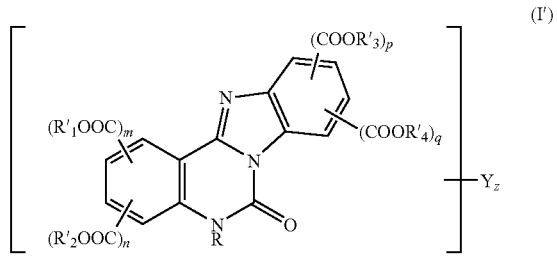

(I')

where R and R'$_1$, R'$_2$, R'$_3$, R'$_4$ are selected independently from the list comprising —H, —CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; m, n, p and q is 0 or 1; (m+n+p+q) is equal or more than 1; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4.

The present invention relates to the synthesis of organic compounds suitable for manufacturing optical films. Carboxy derivatives of heterocyclic molecules comprising several conjugated aromatic and heteroaromatic rings are considered to provide necessary properties of the films for the aforementioned purpose. 6,7-Dihydrobenzimidazo[1,2-c]quinazolin-6-one-9-carboxylic acids and their esters are thought to be of considerable interest in biological processes and are considered to be suitable for photographic applications as well.

The disclosed organic compounds offer the option of special arrangement of molecules in deposited films. One of the exemplary applications is a multilayer film in which organic molecules are linked by the in-plane H-bonds and the off-plane (vertical) π-π bonds. The π-π bonds stimulate stacking of planar molecular nuclei, while the H-bonds may provide interaction between adjacent stacks.

The structure of the disclosed organic compounds may be characterized by a combination of two specific features: (i) a large heterocyclic system that enables π-π interactions with a tendency to the formation of π-π bonded rodlike supramolecules, and (ii) the presence of one or more carboxylic acid or ester groups that enables H-bonding with the tendency to the formation of H-bonded supramolecules.

The arrangement of carboxylic groups influences the structure of H-bonded supramolecules and produces various structural motifs of various spatial configurations. The use of ammonium ion may be advantageous as it can be removed at the drying stage. Additional treatment of the optical crystal films with solutions of Ca, Ba, Sr, Mg, Ni, Zn, or Mn water-soluble salts is advantageous as this renders the films water-insoluble and imparts them with a high environmental stability.

In one preferred embodiment of the disclosed invention, the 6,7-dihydrobenzimidazo[1,2-c]quinazolin-6-one carboxylic acids and esters thereof have the general structural formula from the group comprising structures 1 to 36 given in the Table.

TABLE

Examples of 6,7-dihydrobenzimidazo[1,2-c]quinazolin-6-one carboxylic acids and esters thereof TABLE-continued
Examples of 6,7-dihydrobenzimidazo[1,2-c]quinazolin-6-one carboxylic acids and esters thereof
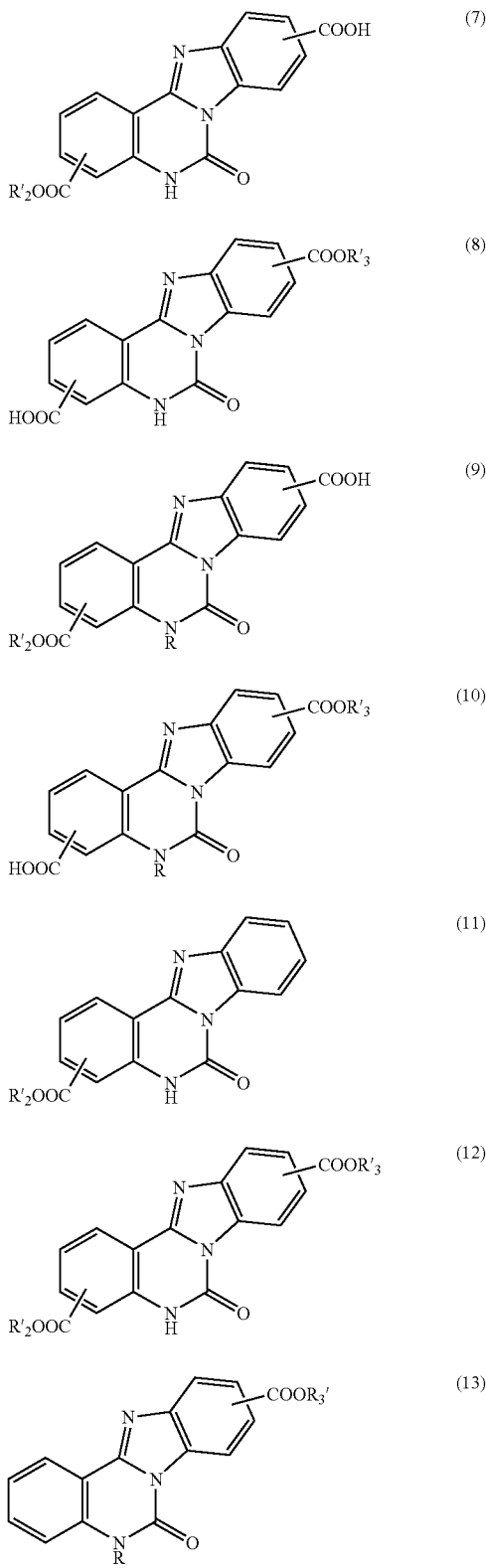
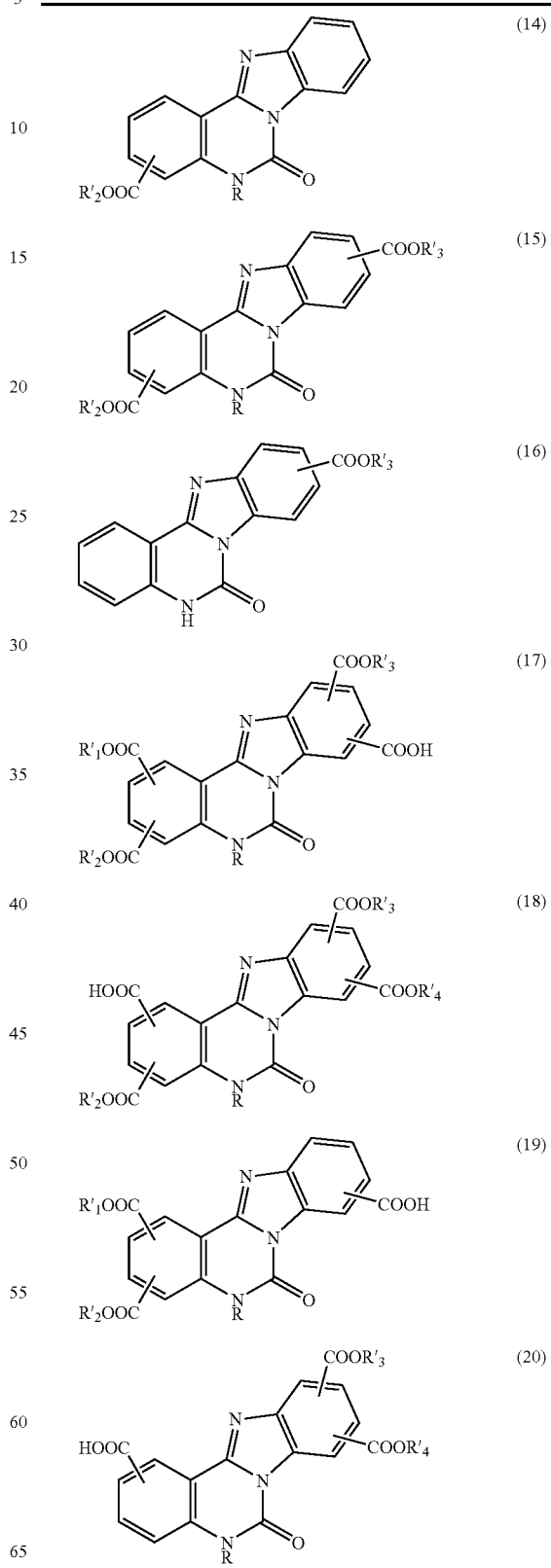

TABLE-continued
Examples of 6,7-dihydrobenzimidazo[1,2-c]quinazolin-6-one carboxylic acids and esters thereof
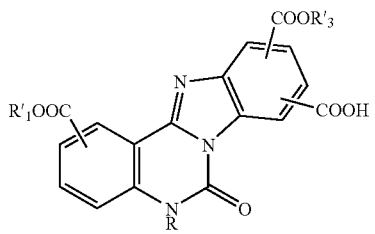 (21)
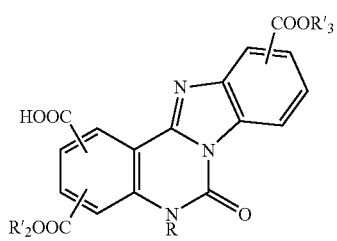 (22)
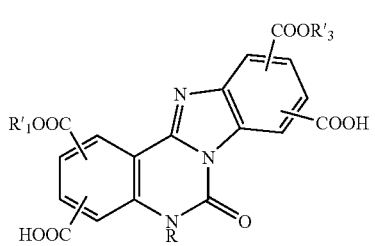 (23)
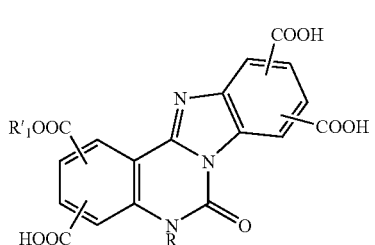 (24)
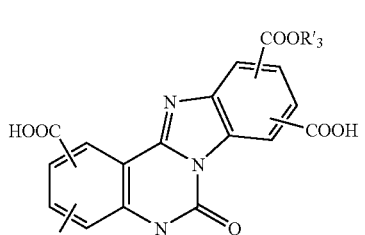 (25)
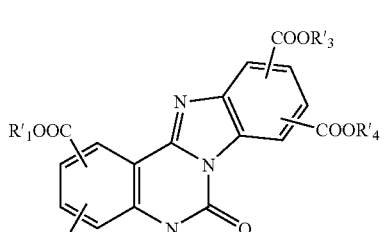 (26)
TABLE-continued
Examples of 6,7-dihydrobenzimidazo[1,2-c]quinazolin-6-one carboxylic acids and esters thereof
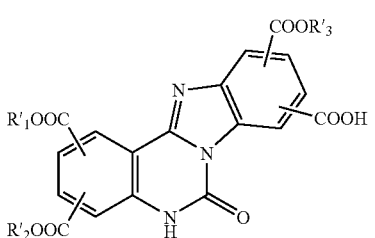 (27)
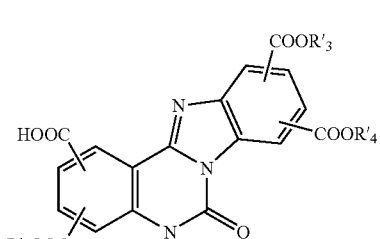 (28)
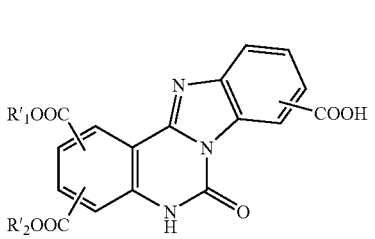 (29)
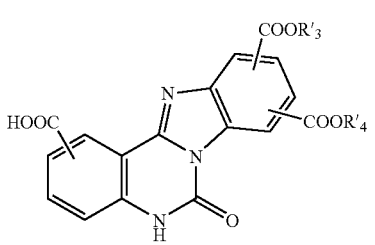 (30)
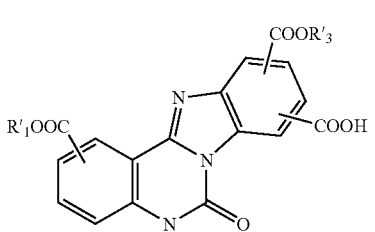 (31)
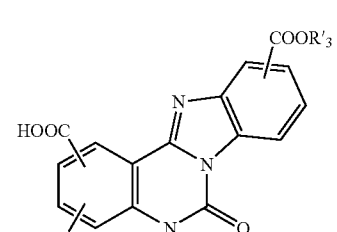 (32)

TABLE-continued

Examples of 6,7-dihydrobenzimidazo[1,2-c]quinazolin-6-one carboxylic acids and esters thereof

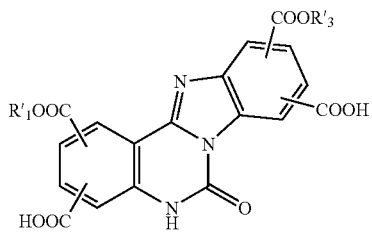
(33)

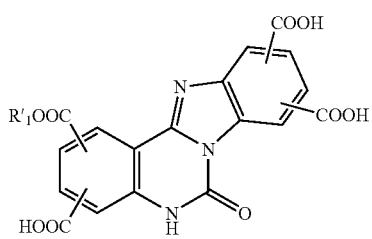
(34)

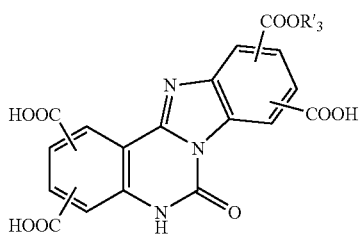
(35)

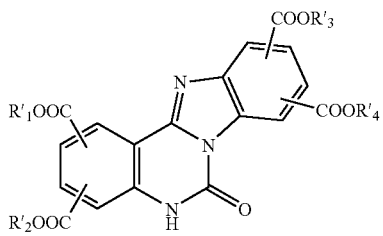
(36)

In one preferred embodiment of the present invention, the compound comprises one or more carboxylic acid groups. In another preferred embodiment of the present invention, the compound comprises one or more carboxylic acid groups and one or more ester groups. In still another preferred embodiment of the present invention, the compound comprises one or more ester groups. In yet another preferred embodiment of the present invention, the compound is selected from 6,7-dihydrobenzimidazo[1,2-c]quinazolin-6-one-9-carboxylic acid, 6,7-dihydrobenzimidazo[1,2-c]quinazolin-6-one-10-carboxylic acid and methyl esters thereof.

In another preferred embodiment, the present invention provides a method of synthesis of a 6,7-dihydrobenzimidazo[1,2-c]quinazolin-6-one carboxylic acid and esters thereof of the general structural formula

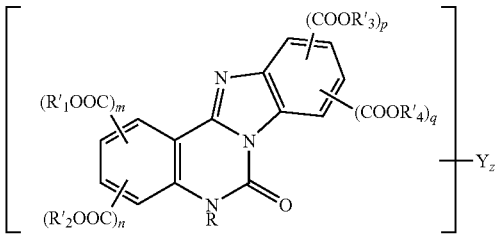
(I′)

where R and $R'_1$, $R'_2$, $R'_3$, $R'_4$ are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; m, n, p and q is 0 or 1; (m+n+p+q) is equal or more than 1; Y is a substituent selected from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$; and z is 0, 1, 2, 3 or 4, which method comprises the step of reacting in the presence of an oxidant a component of the formula (II′):

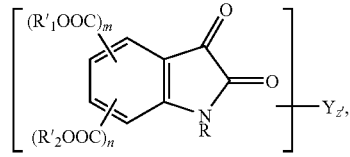
(II′)

where z′ is 0, 1 or 2; with a component of the formula (III′):

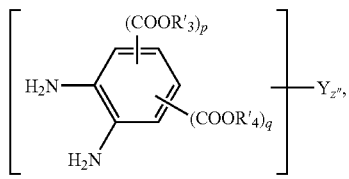
(III′)

where z″ is 0, 1 or 2.

In still another preferred embodiment, the present invention provides a method of the synthesis of a 6,7-dihydrobenzimidazo[1,2-c]quinazolin-6-one carboxylic acid and esters thereof of the general structural formula

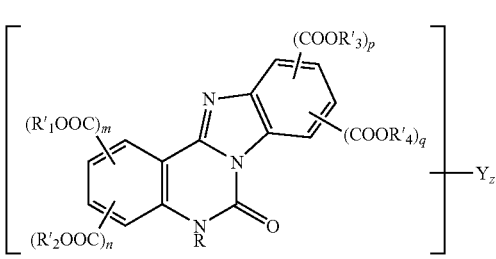
(I′)

where R and $R'_1$, $R'_2$, $R'_3$, $R'_4$ are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; m, n, p and q is 0 or 1; (m+n+p+q) is equal or more than 1; Y is a substituent selected from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$; and z is 0, 1, 2, 3 or 4, which method comprises the step of:

(a) preparing a mixture comprising a solvent; a component selected from the group including isatin and its derivatives of the general structural formula (II'),

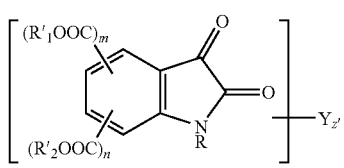

(II')

where z' is 0, 1 or 2;

and a component selected from the group consisting of o-phenylenediamine and its derivatives of the general structural formula (III'):

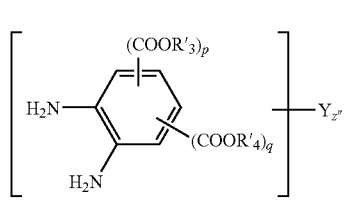

(III')

where z'' is 0, 1 or 2;

(b) treating said mixture with an oxidant;
(c) allowing the reaction to progress; and
(d) isolating the compound from the reaction mass.

In one embodiment of this method the mixture according item (a) comprises hydrochloric acid. In another embodiment of this method the oxidant according item (b) is an inorganic or organic peroxide.

In yet another preferred embodiment, the present invention provides a method of synthesis of a 6,7-dihydrobenzimidazo[1,2-c]quinazolin-6-one carboxylic acid and esters thereof of the general structural formula

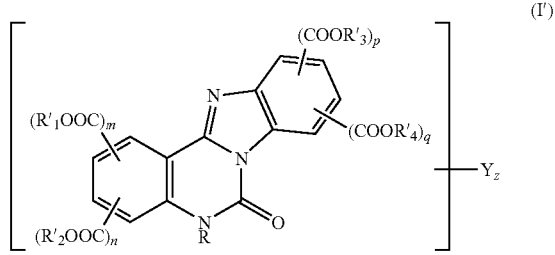

(I')

where R and $R'_1$, $R'_2$, $R'_3$, $R'_4$ are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; m, n, p and q is 0 or 1; (m+n+p+q) is equal or more than 1; Y is a substituent selected from the list comprising, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$; and z is 0, 1, 2, 3 or 4.

The method comprises the following steps:

(a) preparing a mixture consisting of a solvent; hydrochloric acid; a component selected from the group including isatin and its derivatives of the general structural formula (II')

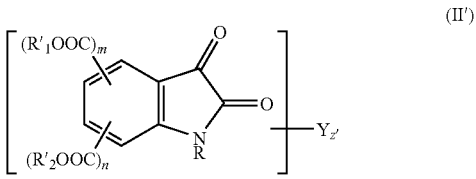

(II')

where z' is 0, 1 or 2;

and a component selected from the group consisting of o-phenylenediamine and its derivatives of the general structural formula (III')

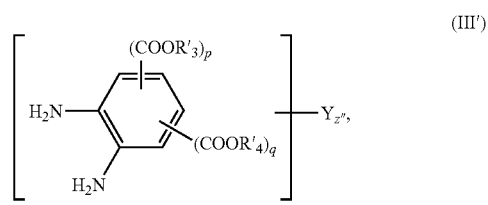

(III')

where z'' is 0, 1 or 2;

(b) treating said mixture with an oxidant selected from the group of inorganic and organic peroxides at a reaction temperature not higher than the temperature of side reactions;

(c) stirring the obtained reaction mass at the reaction temperature until the reaction is completed; and (d) isolating the compound from the reaction mass.

In one preferred embodiment of the disclosed method, the molar ratio of components (II) or (II') and (III) or (III') is selected in the interval from 1:0.8 to 1:1.2. In another preferred embodiment of the disclosed method, the molar ratio of components (II) or (II') and (III) or (III') is predominantly selected equal to 1:1. In still another preferred embodiment of the disclosed method, the solvent is water. In another preferred embodiment of the disclosed invention, the solvent is a mixture of water and acetic acid. In another preferred embodiment of the disclosed invention, the solvent is a mixture of water and dimethylsulfoxide. In another preferred embodiment of the disclosed invention, the solvent is a mixture of water, dimethylsulfoxide, and acetic acid. In another embodiment of the disclosed invention, the content of water in the mixed solvent is not lower than 20%. In still another preferred embodiment of the disclosed invention, the oxidant is peroxyacetic acid ($CH_3COOOH$). In a possible preferred embodiment of the disclosed method, the oxidant is hydrogen peroxide ($H_2O_2$). In another embodiment of the disclosed method, the oxidant is potassium peroxydisulfate ($K_2S_2O_8$).

In a further preferred embodiment of the invention, the oxidant is used in an amount not lower than 0.5 mole per mole of isatin or a derivative thereof of the general structural formula (II) or (II'). In another preferred embodiment, the oxidant is used predominantly in an amount of 1 mole per mole of isatin or derivative thereof of the general structural formula (II) or (II'). In yet another preferred embodiment, the hydrochloric acid is used in an amount selected in the interval from 1 mole to 20 moles per mole of o-phenylenediamine or derivative thereof of the general structural formula (III) or (III'). In another preferred embodiment of the disclosed method, the stage of oxidation further includes the catalytic action of radiation. In one preferred embodiment of the disclosed method, the radiation is white or UV light. In another preferred embodiment of the disclosed method, the radiation is white and UV light. In another preferred embodiment of the disclosed method, the temperature of side reactions is not higher than 60 degrees centigrade. In another embodiment, the present invention provides the method, wherein the oxidant is air. In still another embodiment, the present invention provides the method, wherein the stage of product isolation from the reaction mixture comprises filtering the reaction mass and washing the residue on the filter.

In one preferred embodiment of the disclosed invention the 6,7-dihydrobenzimidazo[1,2-c]quinazoline-6-one carboxylic acids and esters thereof of the general structural formula (I) or (I') are obtainable by any disclosed method.

In yet another aspect of the present invention, there is provided a mixture of at least two compounds (as defined by the general structural formulae (I) or (I') and including those structures 1 to 36 given in the Table, 6,7-dihydrobenzimidazo[1,2-c]quinazolin-6-one-9-carboxylic acid, 6,7-dihydrobenzimidazo[1,2-c]quinazolin-6-one-10-carboxylic acid and methyl esters thereof) obtainable by any disclosed method of the present invention. In an embodiment of the mixture, m, n and q are equal to 0, p is equal to 1, R is H, R' is H; and the position of —COOH on the aromatic ring is different in the two compounds. In another embodiment of the mixture, m, n and q are equal to 0, p is equal to 1, R is $CH_3$, R' is H; and the position of —COOH on the aromatic ring is different in the two compounds.

In another aspect, the disclosed invention provides an anisotropic crystal film comprising a substrate and at least one layer made of at least one carboxylic acid or ester thereof of the general structural formula (I) or (I') or selected from the list comprising structures 1 to 36 given in the Table, 6,7-dihydrobenzimidazo[1,2-c]quinazolin-6-one-9-carboxylic acid, 6,7-dihydrobenzimidazo[1,2-c]quinazolin-6-one-10-carboxylic acid, methyl esters thereof, mixtures of at least two such compounds.

In order that the invention may be more readily understood, reference is made to the following examples, which are intended to be illustrative of the invention, but are not intended to be limiting in scope.

EXAMPLE 1

This example describes the synthesis of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid using peroxyacetic acid as oxidant in a mixture of water and acetic acid.

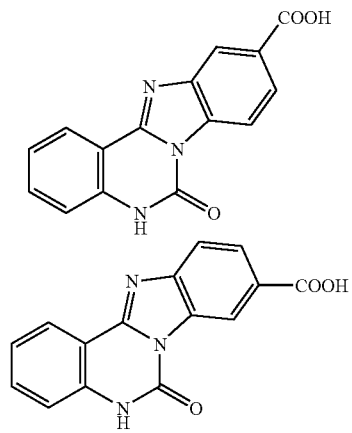

3,4-Diaminobenzoic acid (5.0 g) is dissolved in the mixture of water and hydrochloric acid (84.0 g of water and 3.4 g of 35% aqueous HCl solution) at 20° C. Isatin (4.8 g) is mixed with glacial acetic acid (70.0 g) and water (30.0 g). The solution of 3,4-diaminobenzoic acid is added to the suspension of isatin and the resulting mixture is stirred for 5 min. Then peroxyacetic acid (6.4 g of 39% aqueous $CH_3COOOH$) is added and the reaction mixture is heated to 50° C., kept at this temperature for 20 min, and cooled down to room temperature. The resulting suspension is filtered and the residue is washed on the filter with an aqueous acetic acid solution (50 ml of acetic acid and 100 ml of water). The obtained product is dried in air for 15 h at 100° C. The process yields 6.6 g of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid.

The mass spectrum of the product recorded using a Vision 2000 spectrometer is as follows (m/z, amu): 279.3; mol. wt., 279.06. $^1$H NMR spectrum (Bruker WM-250; DMSO-$d_6$; δ, ppm). 7.39 (q, 2H, 8 Hz); 7.68 (t, 1H, 6 Hz); 7.88 (d, 2H); 8.09 (d, 1H); 8.32 (d, 1H); 8.95 (s, 1H); (isomer mixture). The electronic absorption spectrum of an aqueous solution of the product measured using an Ocean PC 2000 UV/VIS spectrophotometer showed the absorption maxima at $\lambda_{max1}$=325 nm and $\lambda_{max2}$=335-340 nm. The IR absorption spectrum (FSM-1201; η, cm$^{-1}$): 1712 (C=O amide), 1732.2 (C=O carboxy groups). The elemental analyses gave the following results (%): C, 64.52; H, 3.25; N, 15.05 (anal. calcd. for $C_{15}H_9N_3O_3$); C, 64.71; H, 3.13; N, 15.00 (found).

EXAMPLE 2

This example describes the synthesis of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid using hydrogen peroxide as the oxidant in a 10% aqueous hydrochloric acid solution. 3,4-Diaminobenzoic acid (5.0 g) is dissolved in a mixture of water and hydrochloric acid (80.0 g of water and 3.4 g of 35% aqueous HCl solution) at 20° C. Isatin (4.8 grams) is mixed with water (50.0 g) and hydrochloric acid (60 g of 35% aqueous HCl solution). The solution of 3,4-diaminobenzoic acid is added to the isatin suspension and the resulting mixture is stirred for 5 min. Then hydrogen peroxide (3.8 g of 30% aqueous $H_2O_2$) is added and the reaction mixture is heated to 50° C., kept at this temperature for 30 min, and cooled down to room temperature. The resulting suspension is filtered and residue is washed on the filter with water (50 ml). The product is dried in air for 15 h at 100° C. The process yields 7.3 g of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid.

EXAMPLE 3

This example describes the synthesis of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid using potassium peroxydisulfate as the oxidant in a mixture of water and acetic acid.

3,4-Diaminobenzoic acid (5.0 g) is dissolved in a mixture of water and hydrochloric acid (80.0 g of water and 3.4 g of 35% aqueous HCl solution) at 20° C. Isatin (4.8 grams) is mixed with glacial acetic acid (45.0 g), water (50.0 g), and hydrochloric acid (3.4 g of 35% aqueous HCl solution). The solution of 3,4-diaminobenzoic acid is added to the isatin suspension and the resulting mixture is heated to 50° C. Then potassium peroxydisulfate (6.2 g) is added by portions over 30 min at this temperature and the stirring is continued for 30 min, after which the mixture is cooled down to room temperature. The resulting suspension is filtered and the residue on the filter is washed with water (100 ml). The product is dried in air for 15 h at 100° C. The process yields 6.3 g of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid.

EXAMPLE 4

This example describes the synthesis of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid using hydrogen peroxide as the oxidant in an aqueous medium.

3,4-Diaminobenzoic acid (5.0 g) is dissolved in the mixture of water and hydrochloric acid (80.0 g of water and 3.4 g of 35% aqueous HCl solution) at 20° C. Isatin (4.8 grams) is mixed with water (100.0 g) and hydrochloric acid (13.6 g of 35% aqueous HCl solution). The solution of 3,4-diaminobenzoic acid is added to the isatin suspension and the resulting mixture is stirred for 5 min. Then, hydrogen peroxide (3 g of 30% aqueous $H_2O_2$) is added and the reaction mixture is heated to 50° C., kept at this temperature for 40 min, and cooled to room temperature. The resulting suspension is filtered and the residue is washed on the filter with water (50 ml). The product is dried in air for 15 h at 100° C. The process yields 6.6 g of a mixture of 6,7-dihydrobenzimidazo[1,2-c]quinazolin-6-one-9-carboxylic acid and 6,7-dihydrobenzimidazo[1,2-c]quinazolin-6-one-10-carboxylic acid.

EXAMPLE 5

This example describes the synthesis of a mixture of methyl esters of 6,7-dihydrobenzimidazo[1,2-c]quinazolin-6-one-9-carboxylic acid and 6,7-dihydrobenzimidazo[1,2-c]quinazolin-6-one-10-carboxylic acid using peroxyacetic acid as the oxidant.

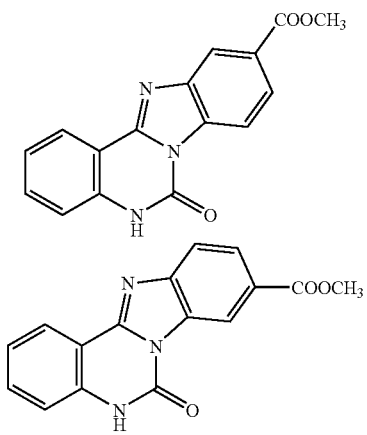

3,4-Diaminobenzoic acid methyl ester (methyl 3,4-diaminobenzoate) (5.0 g) and isatin (4.4 g) are suspended in the mixture of water (120 ml), acetic acid (30 ml), and HCl (6.2 g of 35% aqueous HCl solution) for 5 min. Then peroxyacetic acid (6.5 g of 39% aqueous $CH_3COOOH$) is added and the reaction mixture is heated to 50° C. and stirred at this temperature for 30 min; then the temperature is increased to 70° C., the mixture is treated for 30 min, and cooled down to room temperature. The resulting suspension is filtered and the residue on the filter is washed with aqueous acetic acid solution (50 ml of acetic acid and 100 ml of water). The product is dried in air for 15 h at 100° C. The process yields 5.6 g of a mixture of methyl esters of 6,7-dihydrobenzimidazo[1,2-c]quinazolin-6-one-9-carboxylic acid and 6,7-dihydrobenzimidazo[1,2-c]quinazolin-6-one-10-carboxylic acid.

The mass spectrum of the product recorded using a Vision 2000 spectrometer is as follows (m/z, amu): 293; mol. wt., 293.08; $^1$H NMR (Bruker WM-250; DMSO-$d_6$; δ, ppm): 3.9(s, 6H); 7.39 (m, 4H,); 7.68 (q, 2H,); 7.90 (d, 1H); 8.09 (t, 2H); 8.30 (s, 1H); 8.35 (d, 2H); 8.42 (d, 1H); 8.94 (s, 1H); 12.0 (s, 1H); 12.1 (s, 1H) (isomer mixture). The electronic absorption spectrum of an aqueous solution of the product measured using an Ocean PC 2000 UV/VIS spectrophotometer showed the absorption maxima at $\lambda_{max1}$=325 nm and $\lambda_{max2}$=335-340 nm. The IR absorption spectrum (FSM-1201; η, cm$^{-1}$): 1712 (C=O amide), 1730.0 (C=O ester groups). The elemental analyses gave the following results (%): C, 65.53; H, 3.78; N, 14.33 (anal. calcd. for $C_{16}H_{11}N_3O_3$); C, 65.60; H, 3.53; N, 14.26 (found).

The invention claimed is:
1. A 6,7-dihydrobenzimidazo[1,2-c]quinazoline-6-one carboxylic acid and its esters of the general structural formula

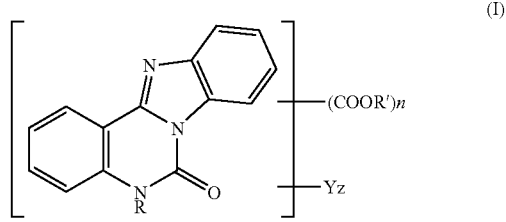

(I)

where R and each R' are selected independently from the list comprising —H, —CH$_3$, —C$_2$H$_5$, —C$_3$H$_7$, -iso- $C_3H_7$, —$CH_2CH_2CH_2CH_3$, —$CH(CH_3)CH_2CH_3$, —$CH_2CH(CH_3)CH_3$ and —$C(CH_3)_3$, n is 1, 2, 3 or 4, Y is a substituent selected independently from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$, and z is 0, 1, 2, 3 or 4.

2. A compound according to claim 1 of the general structural formula $$\left[ \begin{array}{c} (R'_1OOC)_m \\ (R'_2OOC)_n \end{array} \stackrel{(COOR'_3)_p}{\underset{R}{\bigotimes}} (COOR'_4)_q \right] - Y_z \quad (I')$$

where R and $R'_1$, $R'_2$, $R'_3$, $R'_4$ are selected independently from the list comprising —H, —$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$;

m, n, p and q is 0 or 1;

(m+n+p+q) is equal or more than 1;

Y is a substituent selected independently from the list comprising —$CH_3$, —$C_2H_5$, —$NO_2$, —Cl, —Br, —F, —$CF_3$, —CN, —OH, —$OCH_3$, —$OC_2H_5$, —$OCOCH_3$, —OCN, —SCN, —$NH_2$, —$NHCOCH_3$, and z is 0, 1, 2, 3 or 4.

3. A compound according to claim 1, having the general structural formula from the group comprising structures 1 to 36:

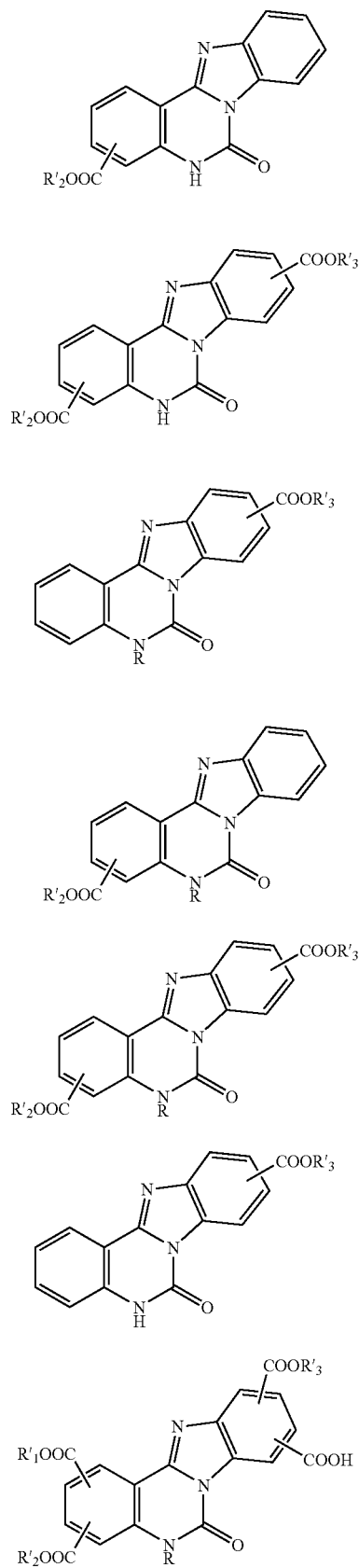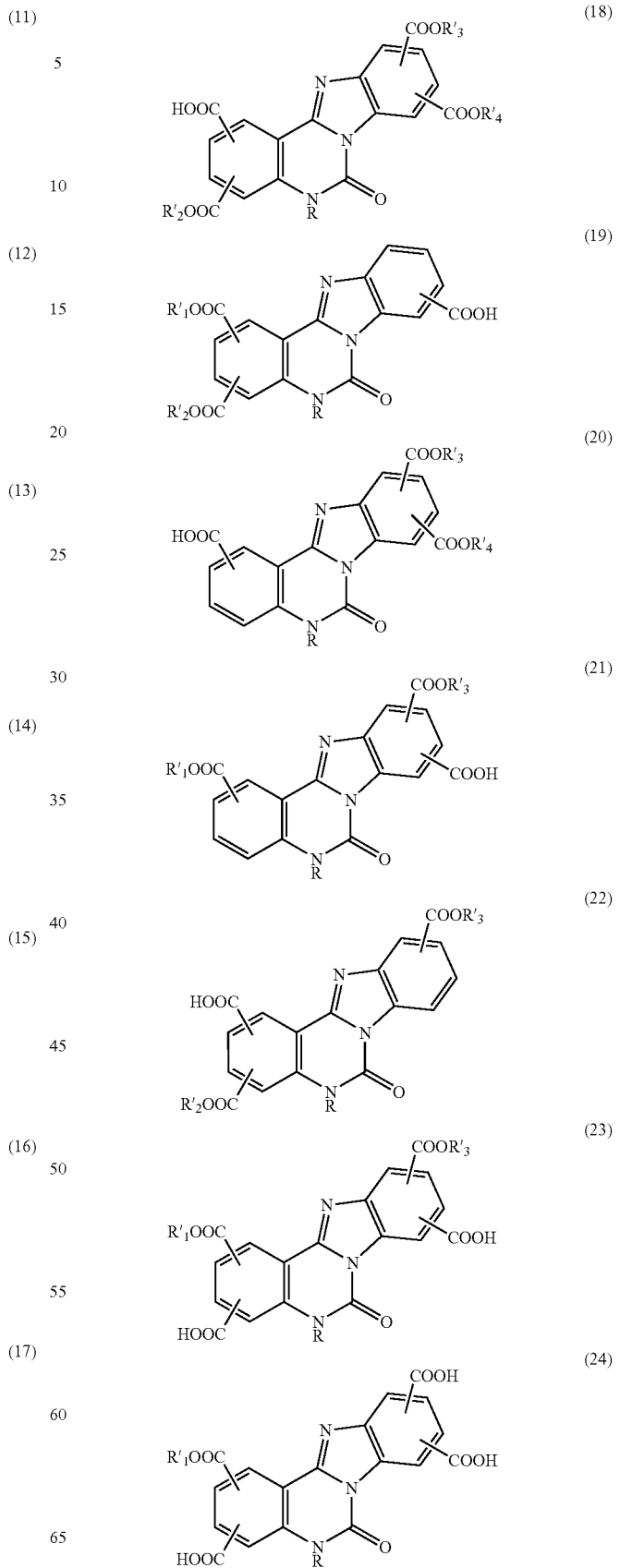

-continued
(25) 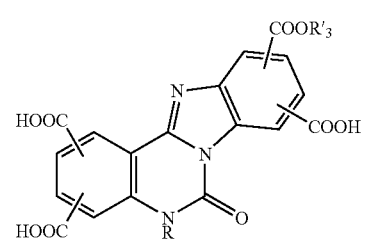
(26) 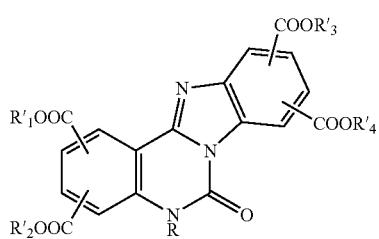
(27) 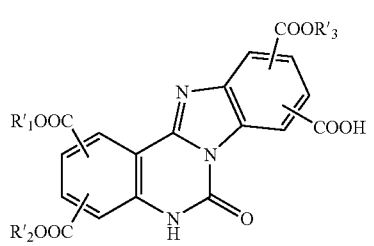
(28) 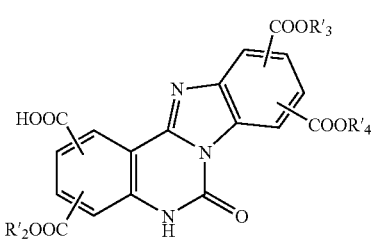
(29) 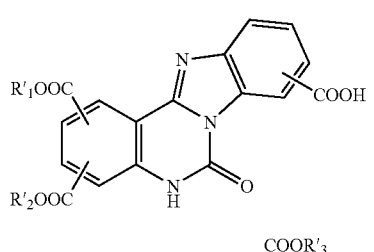
(30) 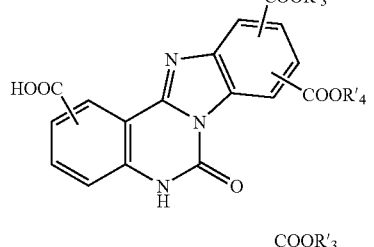
(31) 
-continued
(32) 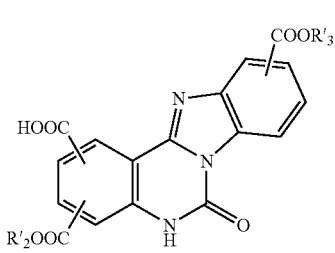
(33) 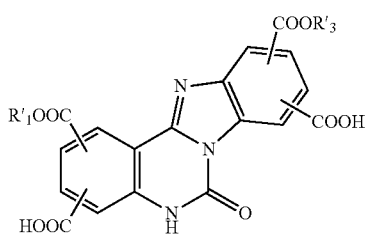
(34) 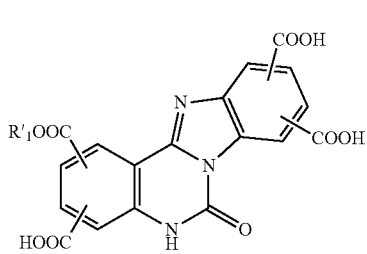
(35) 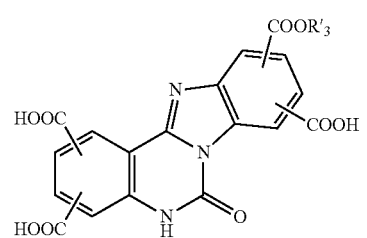
(36) 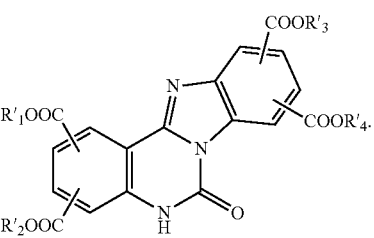
4. A compound according to claim 1, selected from 6,7-dihydrobenzimidazo[1,2-c]quinazolin-6-one-9-carboxylic acid, 6,7-dihydrobenzimidazo[1,2-c]quinazolin-6-one-10-carboxylic acid and methyl esters thereof.
5. A method for the synthesis of a 6,7-dihydrobenzimidazo[1,2-c]quinazolin-6-one carboxylic acid and its esters of the general structural formula

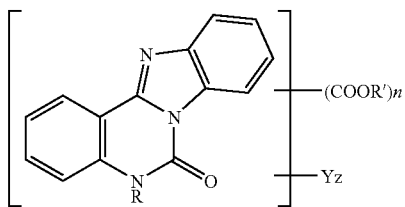

(I)

where R and each R' are selected independently from the list comprising —H,—CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; n is 1, 2, 3 or 4;

Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of reacting in the presence of an oxidant a component of the formula (II):

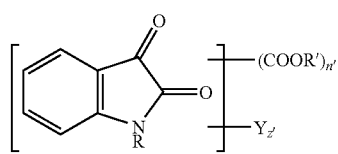

(II)

where n' is 0, 1 or 2, z' is 0, 1 or 2;
with a component of the formula (III):

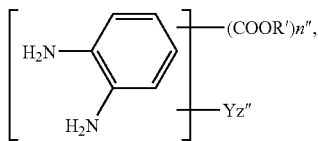

(III)

where n" is 0, 1 or 2, z" is 0, 1 or 2, and n'+n"≧1.

6. A method according to claim 5 for the synthesis of a 6,7—dihydrobenzimidazo[1,2-c]quinazolin-6-one carboxylic acid or an ester thereof of the general structural formula

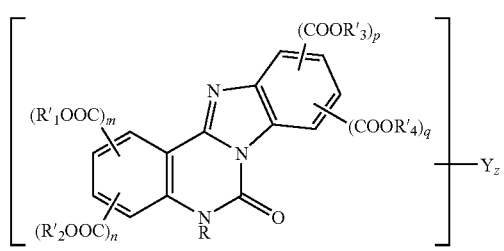

(I')

where R and R'$_1$, R'$_2$, R'$_3$, R'$_4$ are selected independently from the list comprising —H,—CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$;
m, n, p and q is 0 or 1;
(m+n+p+q) is equal or more than 1;

Y is a substituent selected from the list comprising —CH$_3$, —C$_2$H$_5$, —NO$_2$, —Cl, —Br, —F, —CF$_3$, —CN, —OH, —OCH$_3$, —C$_2$H$_5$, —OCOCH$_3$, —OCN, —SCN, —NH$_2$, —NHCOCH$_3$; and z is 0, 1, 2, 3 or 4, which method comprises the step of reacting in the presence of an oxidant a component of the formula (II'):

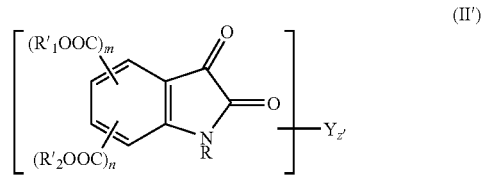

(II')

where z' is 0, 1 or 2;
with a component of the formula (III'):

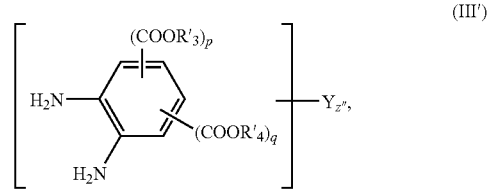

(III')

where z" is 0, 1 or 2.

7. A method for the synthesis of a 6,7-dihydrobenzimidazo[1,2-c]quinazolin-6-one carboxylic acid and its esters of the general structural formula

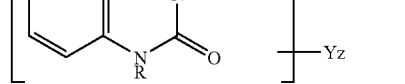

(I)

where R and each R' are selected independently from the list comprising —H,—CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; n is 1, 2, 3 or 4; Y is a substituent selected from the list comprising —CH$_3$, —C$_2$H$_5$, —NO$_2$, —Cl, —Br, —F, —CF$_3$, —CN, —OH, —OCH$_3$, -OC$_2$H$_5$, —OCOCH$_3$, —OCN, —SCN, —NH$_2$, —NHCOCH$_3$; and z is 0, 1, 2, 3 or 4, which method comprises the step of:
(a) preparing a mixture comprising a solvent; a component selected from the group including isatin and its derivatives of the general structural formula (II),

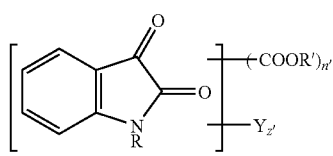

(II)

where n' is 0, 1 or 2, and z' is 0, 1 or 2;

and a component selected from the group consisting of o-phenylenediamine and its derivatives of the general structural formula (III):

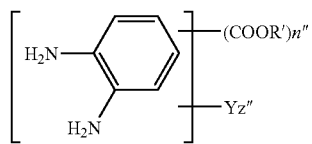

(III)

where n" is 0, 1 or 2, z" is 0, 1 or 2, and n'+n"$\geq$1;

(b) treating said mixture with an oxidant;

(c) allowing the reaction to progress; and (d) isolating the 6,7-dihydrobenzimidazo[1,2-c]quinazolin-6-one carboxylic acid and its esters from the reaction mass.

8. A method according to claim 7 for the synthesis of a 6,7-dihydrobenzimidazo[1,2-c]quinazolin-6-one carboxylic acid or an ester thereof of the general structural formula

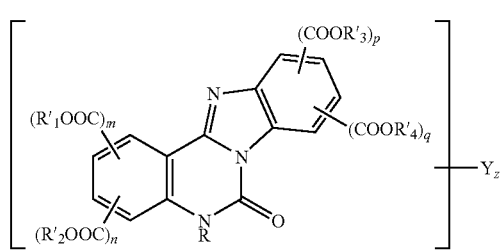

(I')

where R and R'$_1$, R'$_2$, R'$_3$, R'$_4$ are selected independently from the list comprising —H,—CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$; m, n, p and q is 0 or 1; (m+n+p+q) is equal or more than 1; Y is a substituent selected from the list comprising —CH$_3$, —C$_2$H$_5$, —NO$_2$, —Cl, —Br, —F, —CF$_3$, —CN, —OH, —OCH$_3$, —OC$_2$H$_5$, —OCOCH$_3$, —OCN, —SCN, —NH$_2$, —NHCOCH$_3$; and z is 0, 1, 2, 3 or 4, which method comprises the step of:

(a) preparing a mixture comprising a solvent, a component selected from the group including isatin and its derivatives of the general structural formula (II'),

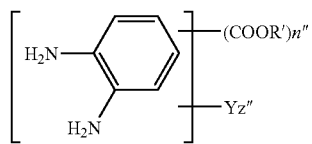

(II')

where z' is 0, 1 or 2;

and a component selected from the group consisting of o-phenylenediamine and its derivatives of the general structural formula (III'):

(III')

where z" is 0, 1 or 2;

(b) treating said mixture with an oxidant;

(c) allowing the reaction to progress; and (d) isolating the 6,7-dihydrobenzimidazo[1,2-c]quinazolin-6-one carboxylic acid and its esters from the reaction mass.

9. A method according to claim 7, wherein the mixture further comprises hydrochloric acid.

10. A method according to claim 7, wherein the oxidant is an inorganic or organic peroxide.

11. A method for the synthesis of a 6,7-dihydrobenzimidazo[1,2-c]quinazolin-6-one carboxylic acid and its esters of the general structural formula

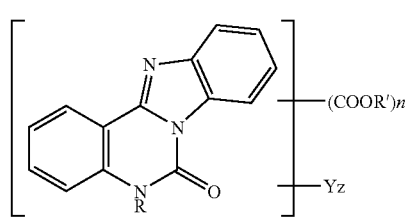

(I)

where R and each R' is selected independently from the list comprising —H,—CH$_3$, —C$_2$H$_5$, —C$_3$H$_7$, -iso-C$_3$H$_7$, —CH$_2$CH$_2$CH$_2$CH$_3$, —CH(CH$_3$)CH$_2$CH$_3$, —CH$_2$CH(CH$_3$)CH$_3$ and —C(CH$_3$)$_3$, n is 1, 2, 3 or 4, Y is a substituent selected from the list comprising —CH$_3$, —C$_2$H$_5$, —NO$_2$, —Cl, —Br, —F, —CF$_3$, —CN, —OH, —OCH$_3$, -OO$_2$H$_5$, —OCOCH$_3$, —OCN, —SCN, —NH$_2$, —NHCOCH$_3$, and z is 0, 1, 2, 3 or 4, which comprises the following steps:

(a) preparing a mixture consisting of a solvent; hydrochloric acid; a component selected from the group including isatin and its derivatives of the general structural formula (II),

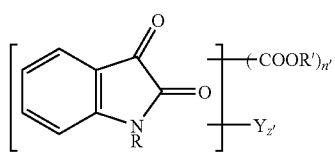

(II)

where n' is 0, 1 or 2, and z' is 0, 1 or 2;

and a component selected from the group consisting of o-phenylenediamine and its derivatives of the general structural formula (III),

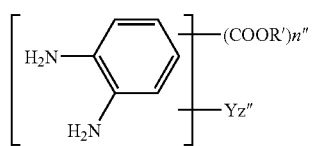

(III)

where n" is 0, 1 or 2, z" is 0, 1 or 2, and $n'+n'' \geqq 1$;

(b) treating said mixture with an oxidant selected from the group of inorganic and organic peroxides at a reaction temperature not higher than the temperature of side reactions;

(c) stirring the obtained reaction mass at the reaction temperature until the reaction is completed; and (d) isolating the compound from the reaction mass.

12. A method according to claim 11 for the synthesis of a 6,7—dihydrobenzimidazo[1,2-c]quinazolin-6-one carboxylic acid or ester thereof of the general structural formula

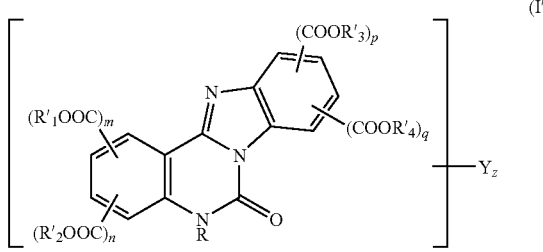

(I')

where R and $R'_1$, $R'_2$, $R'_3$, $R'_4$ are selected independently from the list comprising —H,—$CH_3$, —$C_2H_5$, —$C_3H_7$, -iso-$C_3H_7$, —$CH_2CH_2CH_2CH_3$, —$CH(CH_3)CH_2CH_3$, —$CH_2CH(CH_3)CH_3$ and —$C(CH_3)_3$; m, n, p and q is 0 or 1; (m+n+p+q) is equal or more than 1; Y is a substituent selected from the list comprising —$CH_3$, —$C_2H_5$, —$NO_2$, —Cl, —Br, —F, —$CF_3$, —CN, —OH, —$OCH_3$, -$OO_2H_5$, —$OCOCH_3$, —OCN, —SCN, —$NH_2$, —$NHCOCH_3$, and z is 0, 1, 2, 3 or 4, which comprises the following steps:

(a) preparing a mixture consisting of a solvent; hydrochloric acid; a component selected from the group including isatin and its derivatives of the general structural formula (II'),

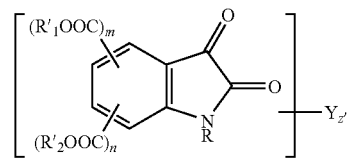

(II')

where z' is 0, 1 or 2;

and a component selected from the group consisting of o-phenylenediamine and its derivatives of the general structural formula (III'),

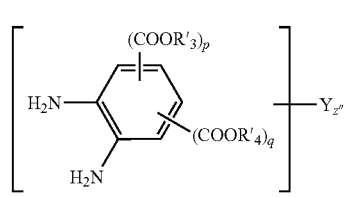

(III')

where z" is 0, 1 or 2;

(b) treating said mixture with an oxidant selected from the group of inorganic and organic peroxides at a reaction temperature not higher than the temperature of side reactions;

(c) stirring the obtained reaction mass at the reaction temperature until the reaction is completed; and (d) isolating the compound from the reaction mass.

13. A method according to claim 7, wherein the solvent is selected from the list comprising water, a mixture of water and acetic acid and a mixture of water and dimethylsulfoxide.

14. A method according to claim 9, wherein the solvent is selected from the list comprising water, a mixture of water and acetic acid and a mixture of water and dimethylsulfoxide.

15. A method according to claim 11, wherein the solvent is selected from the list comprising water, a mixture of water and acetic acid and a mixture of water and dimethylsulfoxide.

16. A method according to claim 5, wherein the oxidant is selected from the list comprising peroxyacetic acid $CH_3COOOH$, hydrogen peroxide $H_2O_2$, and potassium peroxydisulfate $K_2S_2O_8$.

17. A method according to claim 7, wherein the oxidant is selected from the list comprising peroxyacetic acid $CH_3COOOH$, hydrogen peroxide $H_2O_2$, and potassium peroxydisulfate $K_2S_2O_8$.

18. A method according to claim 9, wherein the oxidant is selected from the list comprising peroxyacetic acid $CH_3COOOH$, hydrogen peroxide $H_2O_2$, and potassium peroxydisulfate $K_2S_2O_8$.

19. A method according to claim 11, wherein the oxidant is selected from the list comprising air, peroxyacetic acid $CH_3COOOH$, hydrogen peroxide $H_2O_2$, and potassium peroxydisulfate $K_2S_2O_8$.

20. A method according to claim 5, wherein the stage of oxidation further includes the catalytic action of radiation.

21. A method according to claim 7, wherein the stage of oxidation further includes the catalytic action of radiation.

22. A method according to claim 9, wherein the stage of oxidation further includes the catalytic action of radiation.

23. A method according to claim 11, wherein the stage of oxidation further includes the catalytic action of radiation.

24. A method according to claim 20, wherein said radiation is white and/or UV light.

25. A method according to claim 21, wherein said radiation is white and/or UV light.

26. A method according to claim 22, wherein said radiation is white and/or UV light.

27. A method according to claim 23, wherein said radiation is white and/or UV light.

28. A method according to claim 5, wherein the temperature of side reactions is not higher than 60 degrees centigrade.

29. A method according to claim 7, wherein the temperature of side reactions is not higher than 60 degrees centigrade.

30. A method according to claim 9, wherein the temperature of side reactions is not higher than 60 degrees centigrade.

31. A method according to claim 11, wherein the temperature of side reactions is not higher than 60 degrees centigrade.

32. A method according to claim 7, wherein the step of product isolation from the reaction mass comprises filtering the reaction mass and washing the residue on the filter.

33. A method according to claim 9, wherein the step of product isolation from the reaction mass comprises filtering the reaction mass and washing the residue on the filter.

34. A method according to claim 11, wherein the step of product isolation from the reaction mass comprises filtering the reaction mass and washing the residue on the filter.

35. A compound as defined by claim 1 obtainable by a method as defined in claim 5.

36. A compound as defined by claim 1 obtainable by a method as defined in claim 7.

37. A compound as defined by claim 1 obtainable by a method as defined in claim 9.

38. A compound as defined by claim 1 obtainable by a method as defined in claim 11.

39. A mixture of at least two compounds as defined by claim 1 obtainable by a method as defined in claim 5.

40. A mixture of at least two compounds as defined by claim 1 obtainable by a method as defined in claim 7.

41. A mixture of at least two compounds as defined by claim 1 obtainable by a method as defined in claim 9.

42. A mixture of at least two compounds as defined by claim 1 obtainable by a method as defined in claim 11.

43. A mixture of two compounds according to claim 39, wherein m, n and q are equal to 0, p is equal to 1, R' is H, the position of —COOH on the aromatic ring is different in the two compounds; and R is H or $CH_3$.

44. A mixture of two compounds according to claim 40, wherein m, n and q are equal to 0, p is equal to 1, R' is H, the position of —COOH on the aromatic ring is different in the two compounds; and R is H or $CH_3$.

45. A mixture of two compounds according to claim 41, wherein m, n and q are equal to 0, p is equal to 1, R' is H, the position of —COOH on the aromatic ring is different in the two compounds; and R is H or $CH_3$.

46. A mixture of two compounds according to claim 42, wherein m, n and q are equal to 0, p is equal to 1, R' is H, the position of —COOH on the aromatic ring is different in the two compounds; and R is H or $CH_3$.

47. An anisotropic crystal film comprising a substrate and at least one layer made of at least one compound as defined by claim 1.

48. An anisotropic crystal film comprising a substrate and at least one layer made of at least one compound as defined by claim 35.

49. An anisotropic crystal film comprising a substrate and at least one layer made of at least one compound as defined by claim 36.

50. An anisotropic crystal film comprising a substrate and at least one layer made of at least one compound as defined by claim 37.

51. An anisotropic crystal film comprising a substrate and at least one layer made of at least one compound as defined by claim 38.

52. An anisotropic crystal film comprising a substrate and at least one layer made of at least one compound as defined by claim 39.

53. An anisotropic crystal film comprising a substrate and at least one layer made of at least one compound as defined by claim 40.

54. An anisotropic crystal film comprising a substrate and at least one layer made of at least one compound as defined by claim 41.

55. An anisotropic crystal film comprising a substrate and at least one layer made of at least one compound as defined by claim 42.

* * * * *

UNITED STATES PATENT AND TRADEMARK OFFICE
CERTIFICATE OF CORRECTION

| | | |
|---|---|---|
| PATENT NO. | : 7,888,505 B2 | Page 1 of 4 |
| APPLICATION NO. | : 12/160410 | |
| DATED | : February 15, 2011 | |
| INVENTOR(S) | : Tatyan Doutova et al. | |

It is certified that error appears in the above-identified patent and that said Letters Patent is hereby corrected as shown below:

In the Claims

Column 30, line 53, after "formula" insert --(I)--.

Column 30, line 67, "comprising" should be changed to --consisting of--.

Column 31, line 5, "comprising" should be changed to --consisting of--.

Column 31, line 7, between "-NH2," and "-NHCOCH3," insert --and--.

Column 31, line 11, after "formula" insert --(I')--.

Column 31, line 27, "comprising" should be changed to --consisting of--.

Column 31, line 33, "comprising" should be changed to --consisting of--.

Column 31, line 36, between "-NH2," and "-NHCOCH3," insert --and--.

Column 31, line 38, "claim 1" should be changed to --claim 2--.

Column 31, line 39, "from the group comprising" should be changed to --selected from the group consisting of--.

Column 36, line 67, after "formula" insert --(I)--.

Column 37, line 14, "comprising" should be changed to --consisting of--.

Column 37, line 14, "–H,-CH3, C2H5, C3H 7, -iso-C3H7" should be changed to -- –H, -CH$_3$, -C$_2$H$_5$, -C$_3$H$_7$, -iso-C$_3$H$_7$--.

Signed and Sealed this
Twenty-second Day of September, 2015

Michelle K. Lee
*Director of the United States Patent and Trademark Office*

CERTIFICATE OF CORRECTION (continued)
U.S. Pat. No. 7,888,505 B2

Column 37, line 17, "comprising" should be changed to --consisting of--.

Column 37, line 48, after "formula" insert --(I')--.

Column 37, line 63, "comprising" should be changed to --consisting of--.

Column 38, line 1, "comprising" should be changed to --consisting of--.

Column 38, line 4, between "-NH2," and "-NHCOCH3," insert --and--.

Column 38, line 38, "and its esters" should be changed to --or esters thereof--.

Column 38, line 39, after "formula" insert --(I)--.

Column 38, line 56, "comprising" should be changed to --consisting of--.

Column 38, line 59, "comprising" should be changed to --consisting of--.

Column 38, line 61, between "-NH2," and "-NHCOCH3," insert --and--.

Column 38, line 64, "step" should be changed to --steps--.

Column 38, line 66, "including" should be changed to --consisting of--.

Column 39, line 32, "and its esters" should be changed to --or ester thereof of formula (I)--.

Column 39, line 36, after "formula" insert --(I')--.

Column 39, line 55, "comprising" should be changed to --consisting of--.

Column 39, line 59, "comprising" should be changed to --consisting of--.

Column 39, line 61, between "-NH2," and "-NHCOCH3," insert --and--.

Column 39, line 64, "step" should be changed to --steps--.

Column 39, line 66, "including" should be changed to --consisting of--.

Column 40, line 32, "and its esters" should be changed to --or ester thereof of formula (I')--.

Column 40, line 32, "and its esters" should be changed to --or ester thereof--.

Column 40, line 41, after "formula" insert --(I)--.

Column 40, line 55, "comprising" should be changed to --consisting of--.

Column 40, line 58, "comprising" should be changed to --consisting of--.

Column 40, line 60, "-002H5" should be changed to --$OC_2H_5$--.

Column 40, line 61, between "-NH2," and "-NHCOCH3," insert --and--.

Column 40, line 66, "including" should be changed to --consisting of--.

Column 41, line 29, between "the group" and "of" insert --consisting--.

Column 41, line 29, after "peroxides" insert --,--.

Column 41, line 34, "compound" should be changed to --6,7-dihydrobenzimidazo[1,2-c]quinazolin-6-one carboxylic acid or ester thereof of formula (I)--.

Column 41, line 38, after "formula" insert --(I')--.

Column 41, line 54, "comprising" should be changed to --consisting of--.

Column 41, line 58, "comprising" should be changed to --consisting of--.

Column 41, line 60, "-002H5" should be changed to --$OC_2H_5$--.

Column 41, line 61, between "-NH2," and "-NHCOCH3," insert --and--.

Column 41, line 66, "including" should be changed to --consisting of--.

Column 42, line 33, "compound" should be changed to --6,7-dihydrobenzimidazo[1,2-c]quinazolin-6-one carboxylic acid or ester thereof of formula (I')--.

Column 42, line 35, "comprising" should be changed to --consisting of--.

Column 42, line 38, "comprising" should be changed to --consisting of--.

Column 42, line 41, "comprising" should be changed to --consisting of--.

Column 42, line 44, "comprising" should be changed to --consisting of--.

Column 42, line 48, "comprising" should be changed to --consisting of--.

Column 42, line 52, "comprising" should be changed to --consisting of--.

Column 42, line 56, "comprising" should be changed to --consisting of--.

Column 42, line 61, "the catalytic" should be changed to --a catalytic--.

CERTIFICATE OF CORRECTION (continued)
U.S. Pat. No. 7,888,505 B2

Column 42, line 63, "the catalytic" should be changed to --a catalytic--.

Column 42, line 65, "the catalytic" should be changed to --a catalytic--.

Column 42, line 67, "the catalytic" should be changed to --a catalytic--.

Column 43, line 35, "claim 1" should be changed to --claim 2-- and "claim 5" should be changed to --claim 6--.

Column 43, line 37, "claim 1" should be changed to --claim 2-- and "claim 7" should be changed to --claim 8--.

Column 43, line 39, "claim 1" should be changed to --claim 2-- and "claim 9" should be changed to --claim 10--.

Column 43, line 41, "claim 1" should be changed to --claim 2-- and "claim 11" should be changed to --claim 12--.

Column 44, line 31, "at least one compound" should be changed to --a mixture--.

Column 44, line 34, "at least one compound" should be changed to --a mixture--.

Column 44, line 37, "at least one compound" should be changed to --a mixture--.

Column 44, line 40, "at least one compound" should be changed to --a mixture--.